US011202649B2

(12) United States Patent
Ryan, Jr.

(10) Patent No.: US 11,202,649 B2
(45) Date of Patent: Dec. 21, 2021

(54) SYSTEMS AND METHODS FOR REMOVING MATERIALS FROM THE PANCREAS USING AN ENDOSCOPIC SURGICAL TOOL

(71) Applicant: Interscope, Inc., Whitinsville, MA (US)

(72) Inventor: Jeffery B. Ryan, Jr., Whitinsville, MA (US)

(73) Assignee: INTERSCOPE, INC., Whitinsville, MA (US)

( * ) Notice: Subject to any disclaimer, the term of this patent is extended or adjusted under 35 U.S.C. 154(b) by 190 days.

(21) Appl. No.: 16/428,146

(22) Filed: May 31, 2019

(65) Prior Publication Data

US 2019/0365404 A1 Dec. 5, 2019

Related U.S. Application Data

(60) Provisional application No. 62/679,559, filed on Jun. 1, 2018, provisional application No. 62/682,634, filed on Jun. 8, 2018.

(51) Int. Cl.
*A61B 17/32* (2006.01)
*A61B 17/02* (2006.01)
*A61B 17/00* (2006.01)

(52) U.S. Cl.
CPC .... *A61B 17/32002* (2013.01); *A61B 17/0218* (2013.01); *A61B 2017/00367* (2013.01); *A61B 2017/00477* (2013.01); *A61B 2017/00818* (2013.01); *A61B 2017/320008* (2013.01); *A61B 2017/320028* (2013.01);
(Continued)

(58) Field of Classification Search
CPC ........ A61B 2017/3445; A61B 17/0218; A61B 2017/00367; A61B 2017/320028; A61B 2017/320032; A61B 2217/007; A61B 17/32002; A61B 2017/00818; A61B 2017/320008; A61B 2217/005; A61B 2017/00477; A61B 17/32; A61B 17/02
See application file for complete search history.

(56) References Cited

U.S. PATENT DOCUMENTS 8,012,142 B2    9/2011  Patil et al.
8,882,680 B2   11/2014  Furlong et al.

OTHER PUBLICATIONS

International Search Report and Written Opinion of the International Searching Authority on PCT/US2019/035034 dated Aug. 19, 2019.

(Continued)

*Primary Examiner* — George J Ulsh
*Assistant Examiner* — Arwa Mostafa
(74) *Attorney, Agent, or Firm* — Foley & Lardner LLP

(57) ABSTRACT

A method for removing materials from a subject can include inserting an endoscope into the subject through an esophagus of the subject; introducing, through a cavity wall of a stomach of the subject to access a site within the subject outside the stomach, an endoscopic tool coupled with the endoscope; actuating a cutting assembly of the endoscopic tool to cut material at the site, the material associated with at least one of a pancreatic fluid collection in a pancreas of the subject or an extra-pancreatic fluid collection external to the pancreas; and applying suction to a first end of an aspiration channel of the endoscopic tool to remove the material through the aspiration channel, the aspiration channel extending from the first end to a second end at an opening of the cutting assembly.

14 Claims, 24 Drawing Sheets

(52) U.S. Cl.
CPC ............. *A61B 2017/320032* (2013.01); *A61B 2217/005* (2013.01); *A61B 2217/007* (2013.01)

(56) References Cited

OTHER PUBLICATIONS

Foreign Action other than Search Report for AU Appl. Ser. No. 2019276560 dated May 28, 2021 (3 pages).
International Preliminary Report on Patentability for PCT Appl. Ser. No. PCT/US2019/035034 dated Dec. 10, 2020 (8 pages).

SYSTEMS AND METHODS FOR REMOVING MATERIALS FROM THE PANCREAS USING AN ENDOSCOPIC SURGICAL TOOL

CROSS-REFERENCE TO RELATED APPLICATIONS

The present application claims the benefit of and priority to U.S. Provisional Application No. 62/679,559, titled "METHODS FOR REMOVING MATERIALS FROM THE PANCREAS USING AN ENDOSCOPIC SURGICAL TOOL," filed Jun. 1, 2018, and U.S. Provisional Application No. 62/682,634, titled "METHODS FOR REMOVING MATERIALS FROM THE PANCREAS USING AN ENDOSCOPIC SURGICAL TOOL," filed Jun. 8, 2018, the entire disclosure of which is incorporated herein for any and all purposes.

BACKGROUND

The present disclosure relates generally to pancreatic procedures. More particularly, the present disclosure relates to systems and methods of removing material from the pancreas and peri pancreatic collections using an endoscopic tool.

Acute pancreatitis may run a severe course when pancreatic necrosis becomes infected. In existing procedures, invasive treatment of subjects is typically performed. Existing endoscopic procedures may be limited in the ability to remove necrotic tissue, resulting in time consuming procedures with marginal results and often necessitating multiple procedures.

SUMMARY

The present solution uses an endoscopic tool, such as the ENDOROTOR manufactured by Interscope, Inc. of Whitinsville, Mass., to suck, cut and remove small pieces of tissue in subjects with necrotizing pancreatitis.

At least one aspect relates to a method for removing materials from a subject. The method can include inserting an endoscope into the subject through an esophagus of the subject; introducing, an endoscope via a Natural Orifice Transluminal Endoscopic Surgical (NOTES) procedure referred to as cyst-gastrotomy connecting or anastomosing a peri pancreatic or pancreatic fluid collection to the wall of a stomach of the subject to access a site within the subject outside the stomach, an endoscopic tool coupled with the endoscope; actuating a cutting assembly of the endoscopic tool to cut material at the site, the material associated with at least one of a pancreatic/peri-pancreatic fluid collection in a pancreas of the subject or an extra-pancreatic fluid collection external to the pancreas; and applying suction to a first end of an aspiration channel of the endoscopic tool to remove the material through the aspiration channel, the aspiration channel extending from the first end to a second end at an opening of the cutting assembly.

At least one aspect relates to a system for removing material from a subject. The system can include at least one stent or cyst gastrotomy configured to generate at least one opening to enable access to the material. The material can be associated with at least one of a pancreatic fluid collection in a pancreas of the subject or an extra-pancreatic fluid collection external to the pancreas. The system can include an endoscope that includes an instrument channel and/or an accessory channel disposed outside of the endoscope. The system can include an endoscopic tool coupled with the endoscope. The endoscopic tool can include a cutting assembly comprising an outer cannula and an inner cannula disposed within the outer cannula; a flexible outer tubing coupled to the outer cannula; a flexible torque component including a flexible torque coil or a flexible torque rope, the flexible torque component coupled to the inner cannula and configured to cause the inner cannula to at least one of rotate or reciprocate relative to the outer cannula to remove the material; and an aspiration channel having an aspiration port configured to engage with a vacuum source, the aspiration channel partially defined by an inner wall of the inner cannula and extending from an opening defined in the inner cannula to the aspiration port.

These and other aspects and implementations are discussed in detail below. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification.

BRIEF DESCRIPTION OF THE DRAWINGS

The accompanying drawings are not intended to be drawn to scale. Like reference numbers and designations in the various drawings indicate like elements. For purposes of clarity, not every component can be labeled in every drawing. In the drawings.

DETAILED DESCRIPTION

A. Endoscopic Instrument Systems and Methods

Figure 1A:
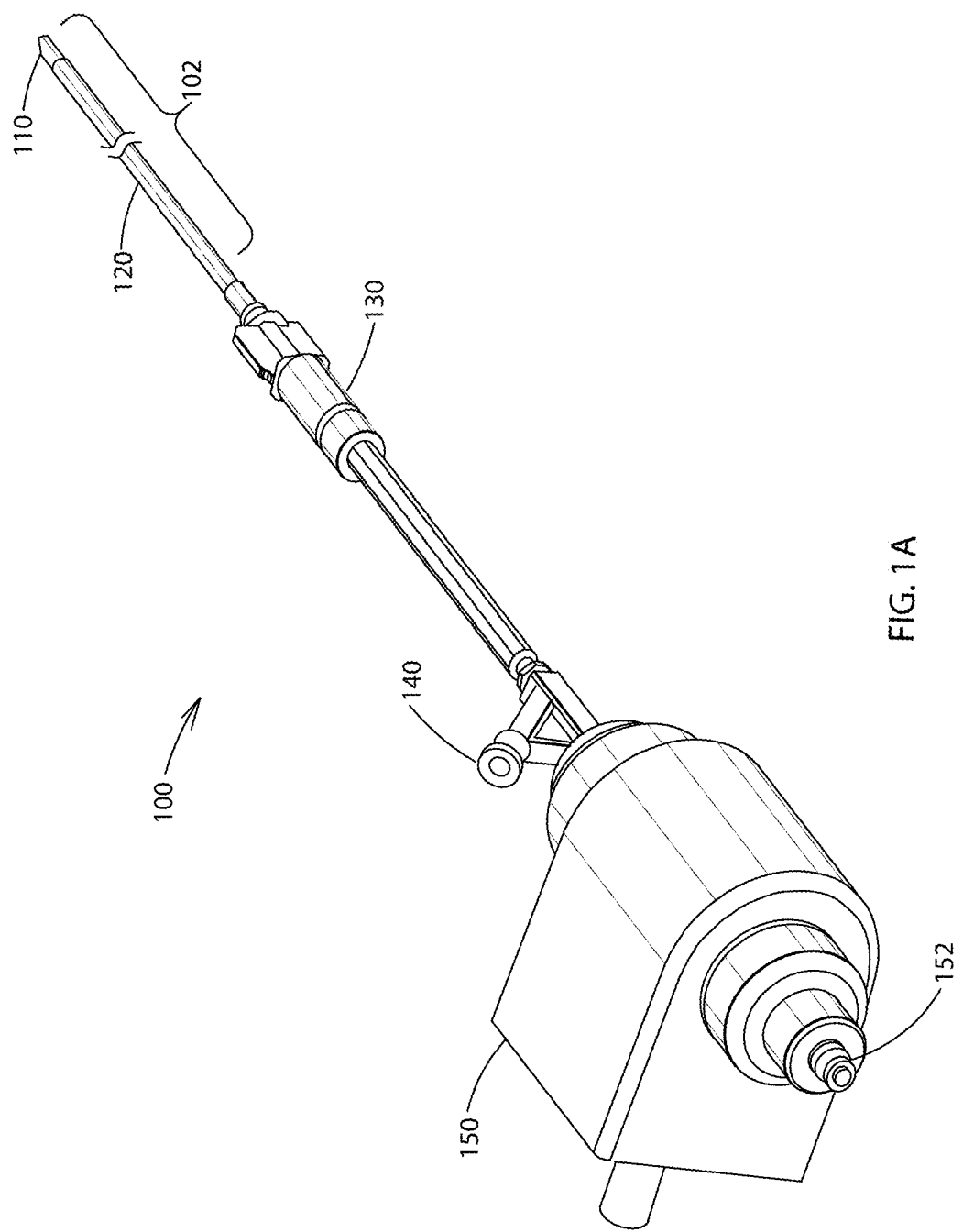
FIG. 1A shows a perspective view of an endoscopic tool and a portion of a drive assembly configured to drive the endoscopic tool according to embodiments of the present disclosure.

Technologies provided herein are directed towards an improved flexible endoscopic instrument that can precisely and efficiently obtain samples of single and multiple polyps and neoplasms from a patient. In particular, the improved endoscopic instrument is capable of debriding samples from one or more polyps and necrotic material, retrieving the debrided samples without having to remove the endoscopic instrument from the treatment site within the patient's body.

The present disclosure will be more completely understood through the following description, which should be read in conjunction with the drawings. In this description, like numbers refer to similar elements within various embodiments of the present disclosure. Within this description, the claims will be explained with respect to embodiments. The skilled artisan will readily appreciate that the methods, apparatus and systems described herein are merely exemplary and that variations can be made without departing from the spirit and scope of the disclosure.

Although the present disclosure is directed towards endoscopic instruments adapted for use with any type of endoscope, for sake of convenience, the teachings of the present disclosure are directed towards endoscopic instruments used with a lower GI scope, such as a colonoscope. It should, however, be appreciated that the scope of the present disclosure is not limited to endoscopic instruments for use with GI scopes, but extends to any type of flexible endoscope, including but not limited to bronchoscopes, gastroscopes and laryngoscopes, or other medical devices that may be used to treat patients.

The endoscopic instrument can include a debriding component that may generally be configured to debride a polyp. Debriding can, for example, include any action involving detaching the polyp or a portion of the polyp from a surface of the patient's body. Accordingly, actions, including but not limited to, cutting, snaring, shredding, slicing, shattering, either entirely or partially, are also examples of debriding. Accordingly, the debriding component may be a component that is capable of cutting, snaring, shredding, slicing, shattering, a polyp from a surface of the patient's body. As such, the debriding component may be implemented as a forceps, scissor, knife, snare, shredder, or any other component that can debride. In some embodiments, the debriding component may be manually actuated such that the debriding component may be operated through the translation of mechanical forces exerted by an operator or automatically actuated, using a turbine, electrical motor, or any other force generating component to actuate the debriding component. For instance, the debriding component may be actuated hydraulically, pneumatically, or electrically. In various embodiments, a separate conduit passing through the tubing or a channel of the endoscope may be configured to carry an electrical wire to provide power to the electrically powered actuator, such as an electrical motor.

The debriding component may be manually operated or may utilize any other means of debriding material such that the debrided material are capable of being retrieved from the surgical site via the suction conduit described above. Accordingly, examples of debriding components may include, but are not limited to, snips, blades, saws, or any other sharp tools that may or may not be driven by a turbine assembly. It should be appreciated that using a debriding component that is able to cut material into small enough pieces may be desirable such that the cut pieces may be retrieved via the suction conduit without having to remove the endoscopic instrument from the endoscope.

An endoscope may be designed to facilitate debriding one or more polyps and necrotic material and removing the debrided material associated in a single operation. In various embodiments, the endoscope may include one or more separate channels for removing debrided material, supplying irrigation fluid, and supplying and removing at least one of pneumatic or hydraulic fluids. In addition, the endoscope may include a debriding component that may be fixedly or removably coupled to one end of the endoscope. In various embodiments, based on the operation of the debriding component, a separate debriding component channel may also be designed for the debriding component. In addition, the endoscope may include a light and a camera. In one embodiment, the endoscope may utilize existing channels to supply pneumatic or hydraulic fluids to the actuator of the endoscopic instrument for actuating the debriding component.

In various embodiments, the endoscopic instrument may be configured to detect the presence of certain layers of tissue. This may be useful for physicians to take extra precautions to prevent bowel perforations while debriding polyps. In some embodiments, the endoscopic instrument may be equipped with a sensor that can communicate with a sensor processing component outside the endoscope to determine the type of tissue based on an impedance difference between tissue. The sensor may gather temperature information as well as density information and provide signals corresponding to such information to the sensor processing unit, which can identify the type of tissue being sensed. In some implementations, the sensor may be an electrical sensor.

In addition, the endoscopic instrument may be equipped with an injectable dye component through which a physician may mark a particular region within the patient's body. In other embodiments, the physician may mark a particular region utilizing the debriding component, without the use of an injectable dye.

Although the present disclosure discloses various embodiments of an endoscopic instrument, including but not limited to a tool that may be attached to the tip of the endoscope, and a tool that may be fed through the length of the endoscope, the scope of the present disclosure is not intended to be limited to such embodiments or to endoscopic instruments in general. Rather, the scope of the present disclosure extends to any device that may debride and remove polyps and or necrotic material from within a patient's body using a single tool. As such, the scope of the present disclosure extends to improved endoscopes that may be built with some or all of the components of the endoscopic instruments described herein. For instance, an improved endoscope with an integrated turbine assembly and configured to be coupled to a debriding component is also disclosed herein. Furthermore, the endoscope may also include predefined conduits that extend through the length of the endoscope such that only the suction conduit may be defined by a disposable tubing, while the air entry and exit conduits and the irrigation conduit are permanently defined within the improved endoscope. In other embodiments, the suction conduit is also predefined but made such that the suction conduit may be cleaned and purified for use with multiple patients. Similarly, the debriding component may also be a part of the endoscope, but also capable of being cleaned and purified for use with multiple patients. Furthermore, it should be understood by those skilled in the art that any or all of the components that constitute the endoscopic instrument may be built into an existing endoscope or into a newly designed endoscope for use in debriding and removing polyps from within the patient's body.

In some implementations, an endoscopic instrument insertable within a single instrument channel of an endoscope can include a power driven instrument head or cutting assembly that is configured to resect material at a site within a subject. The cutting assembly includes an outer cannula and an inner cannula disposed within the outer cannula. The outer cannula defines an opening through which material to be resected enters the cutting assembly. The endoscopic instrument also includes a flexible outer tubing coupled to the outer cannula and configured to cause the outer cannula to rotate relative to the inner cannula. The flexible outer tubing can have an outer diameter that is smaller than the instrument channel in which the endoscopic instrument is insertable. The endoscopic instrument also includes a flexible torque coil having a portion disposed within the flexible outer tubing. The flexible torque coil having a distal end coupled to the inner cannula. The flexible torque coil is configured to cause the inner cannula to rotate relative to the outer cannula. The endoscopic instrument also includes a proximal connector coupled to a proximal end of the flexible torque coil and configured to engage with a drive assembly that is configured to cause the proximal connector, the flexible torque coil and the inner cannula to rotate upon actuation. The endoscopic instrument also includes an aspiration channel having an aspiration port configured to engage with a vacuum source. The aspiration channel is partially defined by an inner wall of the flexible torque coil and an inner wall of the inner cannula and extends from an opening defined in the inner cannula to the aspiration port. The endoscopic instrument also includes an irrigation channel having a first portion defined between an outer wall of the flexible torque coil and an inner wall of the flexible outer tubing and configured to carry irrigation fluid to the aspiration channel.

In some implementations, the proximal connector is hollow and an inner wall of the proximal connector defines a portion of the aspiration channel. In some implementations, the proximal connector is a rigid cylindrical structure and is configured to be positioned within a drive receptacle of the drive assembly. The proximal connector can include a coupler configured to engage with the drive assembly and a tensioning spring configured to bias the inner cannula towards a distal end of the outer cannula. In some implementations, the tensioning spring is sized and biased such that the tensioning spring causes a cutting portion of the inner cannula to be positioned adjacent to the opening of the outer cannula. In some implementations, the proximal connector is rotationally and fluidly coupled to the flexible torque coil. In some implementations, the tensioning spring can be sized and biased such that the distal tip of the inner cannula can contact the inner distal wall of the outer cannula. This may limit any lateral or undesired movement generated due to whip at the distal end of the inner cannula caused by the rotation of the flexible torque coil.

In some implementations, the endoscopic instrument also includes a lavage connector including an irrigation entry port and a tubular member coupled to the lavage connector and the flexible outer tubing. An inner wall of the tubular member and the outer wall of the flexible torque coil can define a second portion of the irrigation channel that is fluidly coupled to the first portion of the irrigation channel. In some implementations, the endoscopic instrument also includes a rotational coupler coupling the flexible outer tubing to the tubular member and configured to cause the flexible outer tubing to rotate relative to the tubular member and cause the opening defined in the outer cannula to rotate relative to the inner cannula. In some implementations, the lavage connector defines an inner bore within which the flexible torque coil is disposed.

In some implementations, the endoscopic instrument also includes a lining within which the flexible torque coil is disposed, the outer wall of the lining configured to define a portion of the irrigation channel. In some implementations, the inner cannula is configured to rotate about a longitudinal axis of the inner cannula and relative to the outer cannula and the aspiration channel is configured to provide a suction force at the opening of the inner cannula.

In some implementations, the flexible torque coil includes a plurality of threads. Each of the plurality of threads can be wound in a direction opposite to a direction in which one or more adjacent threads of the plurality of threads is wound. In some implementations, the flexible torque coil includes a plurality of layers. Each of the plurality of layers can be wound in a direction opposite to a direction in which one or more adjacent layers of the plurality of layers is wound. In some implementations, each layer can include one or more threads. In some implementations, the flexible cable can be made of three separate threads or wires. An inner wire can have a left-hand wound, a middle wire can have a right-hand wound and the outer wire can have a left-hand wound. In some implementations, the inner wire can have a right-hand wound, a middle wire can have a left-hand wound and the outer wire can have a right-hand wound. In some implementations, the flexible cable can be made of two separate threads or wires. In some such implementations, the inner wire can have a left-hand wound and the outer wire can have a right-hand wound. In some other implementations, the inner wire can have a right-hand wound and the outer wire can have a left-hand wound. In some implementations, the wire rope strands can be twisted in either Z-lay or S-lay. Examples of flexible cables include wire ropes and torque coils manufactured by ASAHI INTECC. In some implementations, the outer diameter of the torque rope or coil is limited by the size of the working channel of the endoscope with which the endoscopic tool will be used. Other size considerations that need to be taken into account include providing enough space for the aspiration channel, irrigation channel, amongst others. In some implementations, the outer diameter of the torque coil or torque rope can range between 0.1 mm and 4 mm. In some implementations, the torque coil or rope can have an outer diameter of 0.5 mm to 2.0 mm.

In some implementations, the flexible outer tubing has a length that exceeds the length of the endoscope in which the endoscopic instrument is insertable. In some implementations, the flexible outer tubing has a length that is at least 100 times larger than an outer diameter of the flexible outer tubing. In some implementations, the flexible portion is at least 40 times as long as the cutting assembly.

Figure 1B:
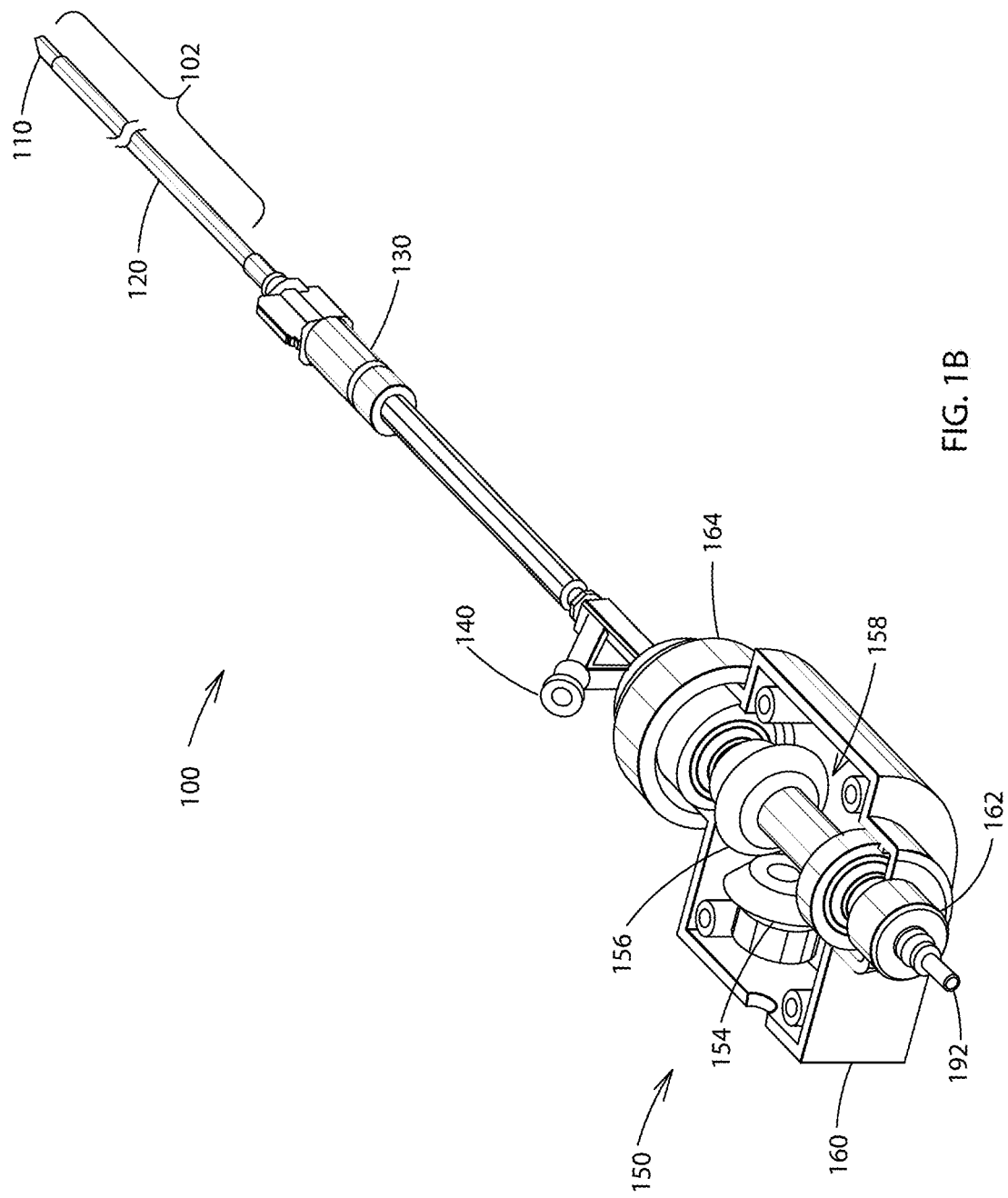
FIG. 1B shows a perspective view of the endoscopic tool and the portion of the drive assembly configured to drive the endoscopic tool shown in FIG. 1A according to embodiments of the present disclosure.
Figure 2:
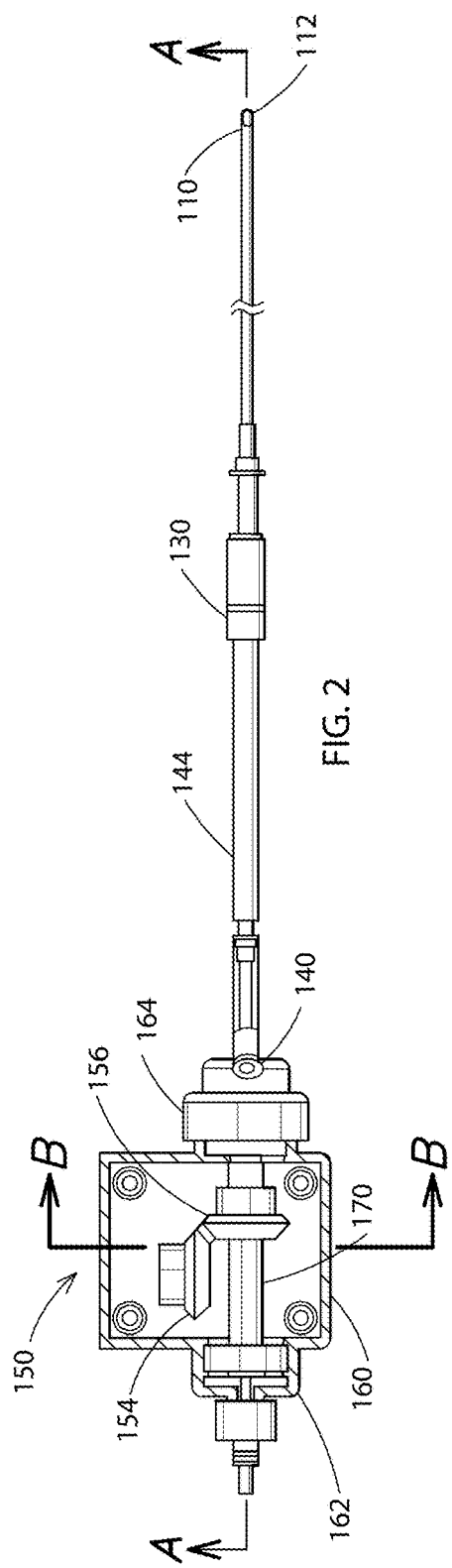
FIG. 2 shows a top view of the endoscopic tool and a top exposed view of the portion of the drive assembly shown in FIGS. 1A-1B according to embodiments of the present disclosure.
Figure 3:
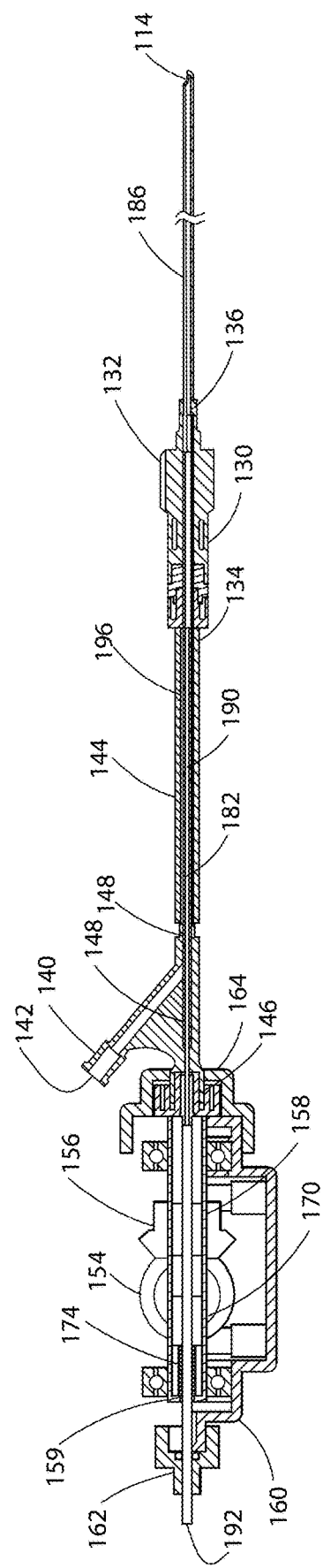
FIG. 3 shows a cross-sectional view of the endoscopic tool and the portion of the drive assembly across the section A-A shown in FIGS. 1A-1B according to embodiments of the present disclosure.
Figure 4:
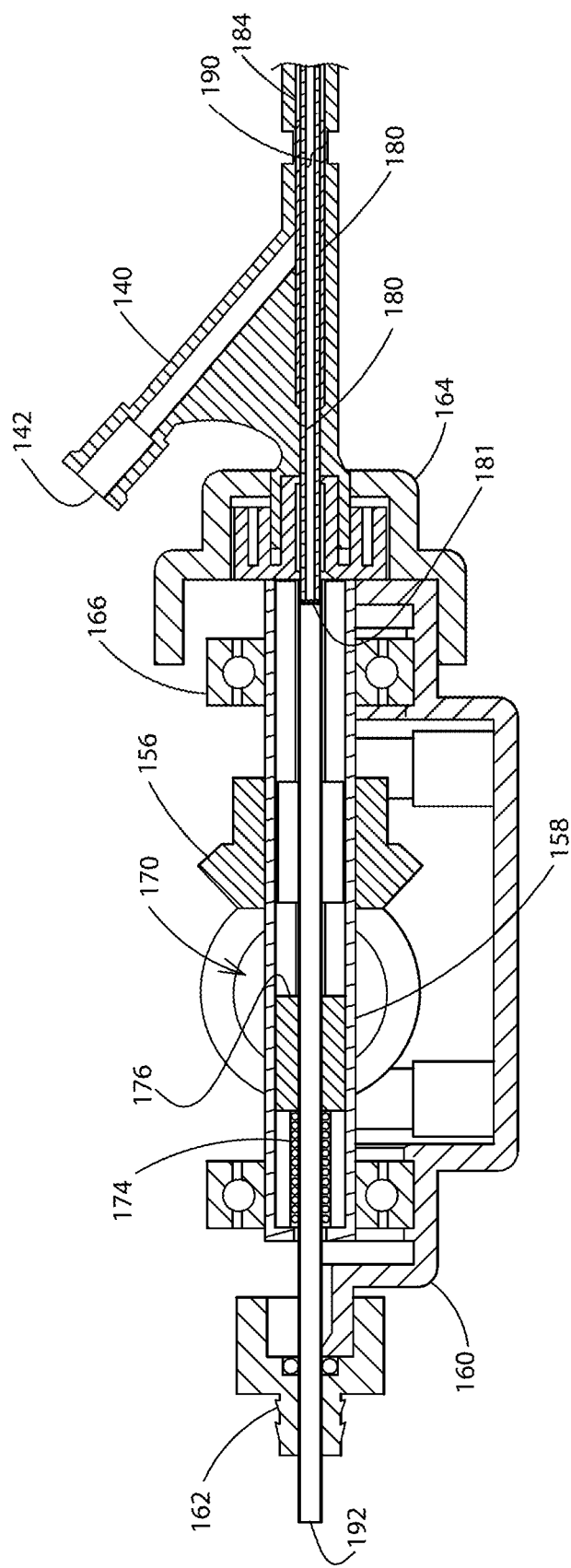
FIG. 4 shows an enlarged view of the drive connector of the endoscope and the portion of the drive assembly shown in FIGS. 1A-1B according to embodiments of the present disclosure.
Figure 5:
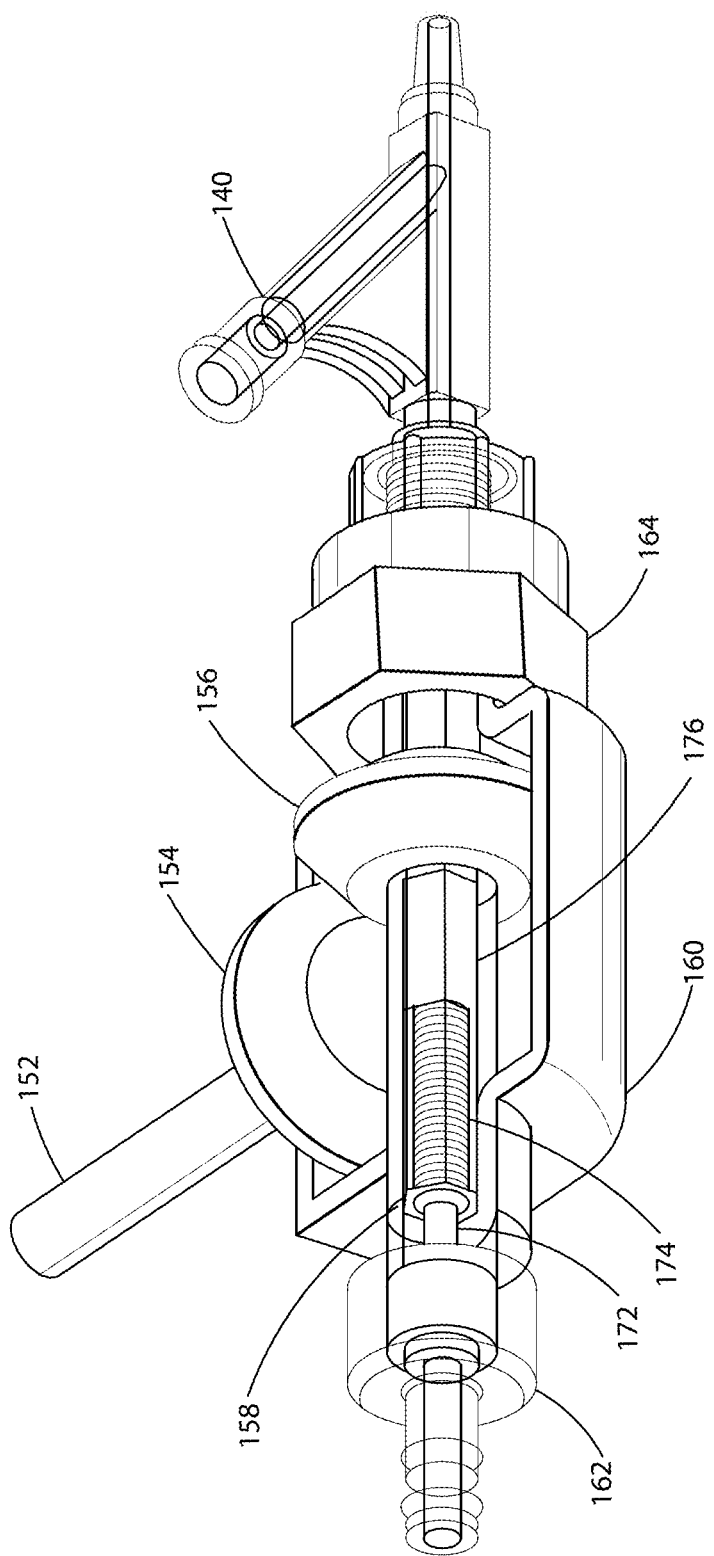
FIG. 5 shows a perspective view of the endoscopic tool and a portion of the drive assembly shown in FIGS. 1A-1B according to embodiments of the present disclosure.
Figure 6:
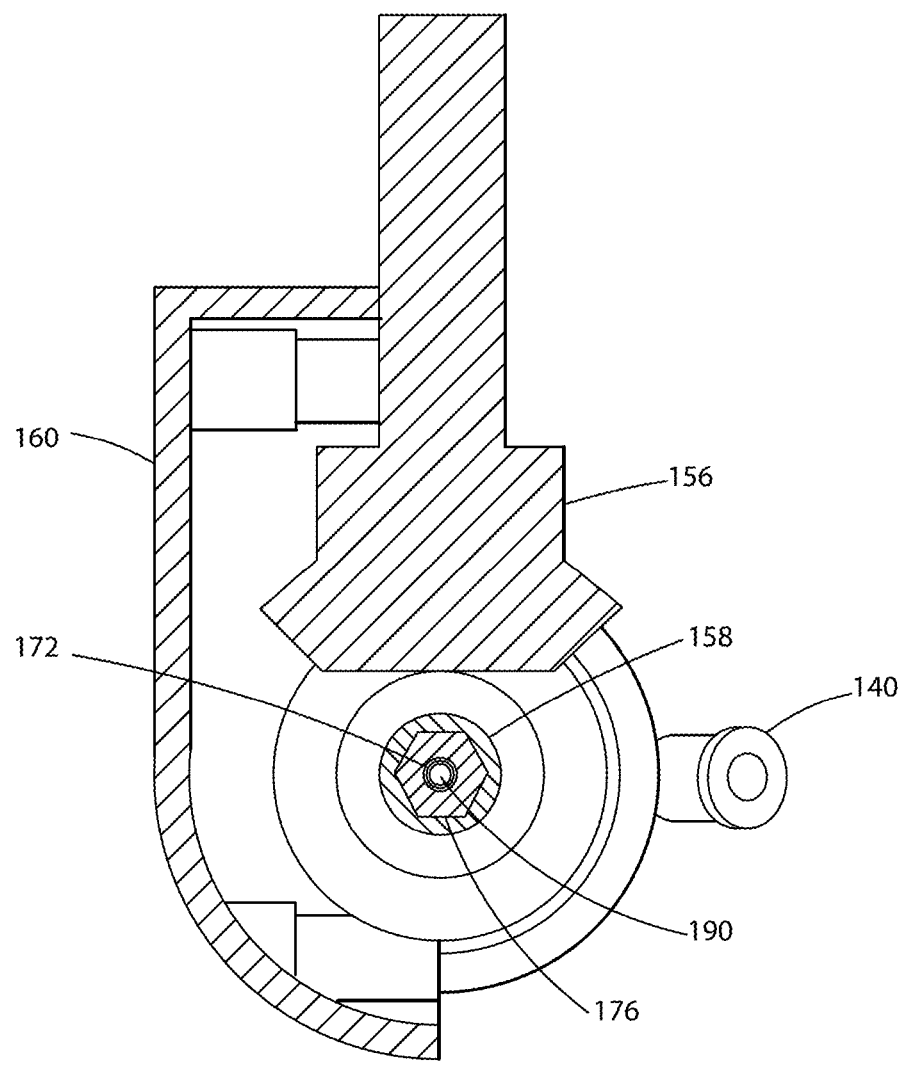
FIG. 6 shows a cross-sectional view of the endoscopic tool and the portion of the drive assembly across the section B-B according to embodiments of the present disclosure.
Figure 7:
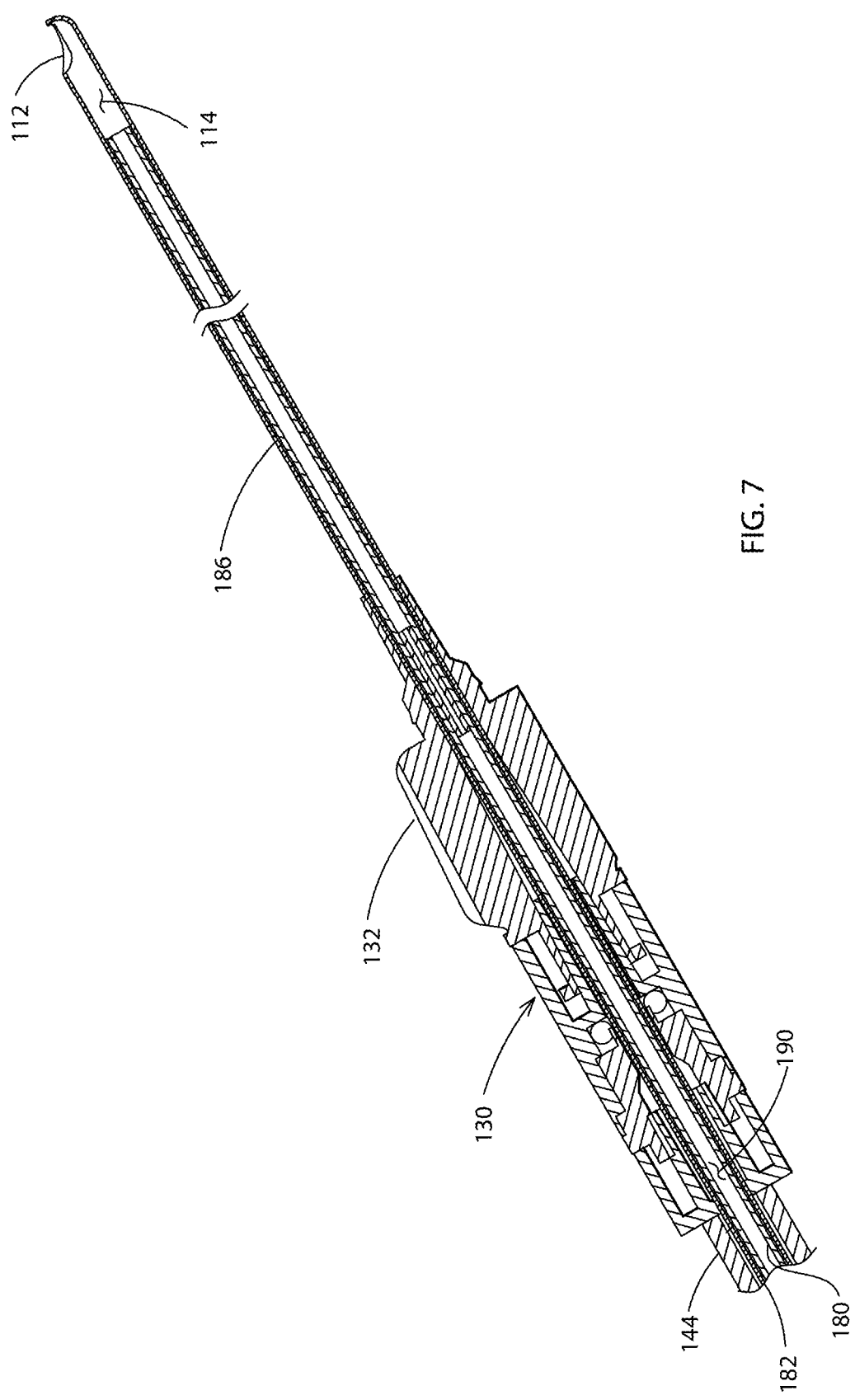
FIG. 7 shows an enlarged cross-sectional view of the rotational coupler section of the endoscopic tool according to embodiments of the present disclosure.
Figure 8A:
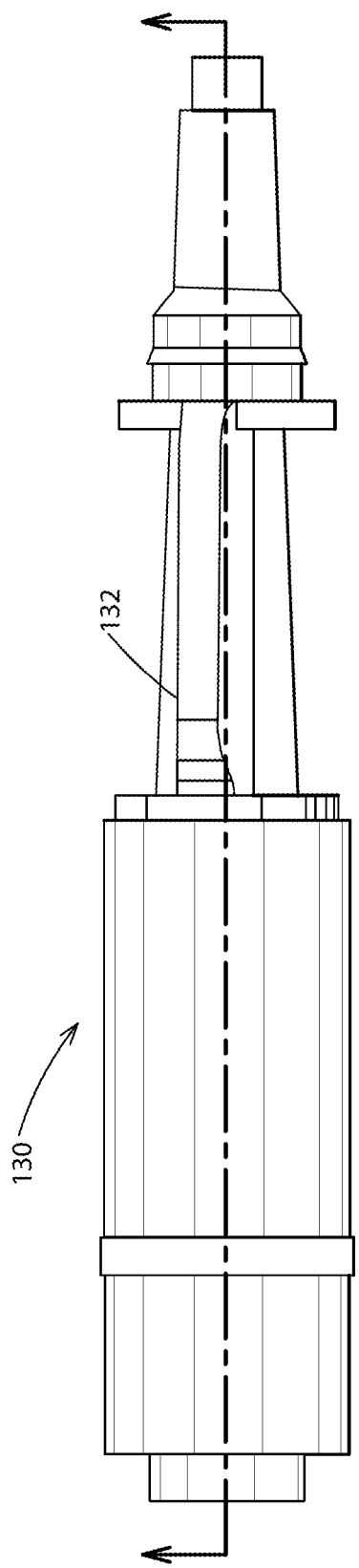
FIG. 8A and FIG. 8B show a top view and a cross-sectional view of the rotational coupler of the endoscopic tool according to embodiments of the present disclosure.
Figure 8B:
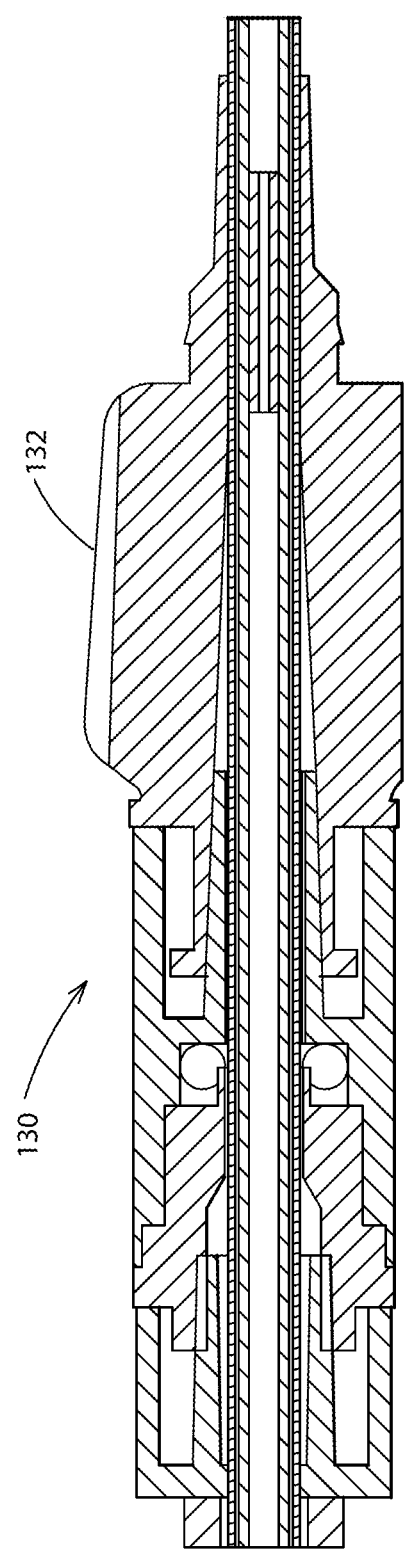

FIGS. 1A-1B show a perspective view of an endoscopic tool 100 and a portion of a drive assembly 150 configured to drive the endoscopic tool. FIG. 1B shows a perspective view of the endoscopic tool and the portion of the drive assembly configured to drive the endoscopic tool shown in FIGS. 1A-1B. Referring now also to FIGS. 2, 3, and 4, FIG. 2 shows a top view of the endoscopic tool 100 and a top exposed view of the portion of the drive assembly 150 shown in FIGS. 1A-1B. FIG. 3 shows a cross-sectional view of the endoscopic tool 100 and the portion of the drive assembly 150 across the section A-A. FIG. 4 shows an enlarged view of the drive connector of the endoscope and the portion of the drive assembly 150. FIG. 5 shows a perspective view of the endoscopic tool 100 and a portion of the drive assembly shown in FIGS. 1A-1B. FIG. 6 shows a cross-sectional view of the endoscopic tool and the portion of the drive assembly across the section B-B. FIG. 7 shows an enlarged cross-sectional view of the rotational coupler section of the endoscopic tool. FIG. 8A and FIG. 8B show a top view and a cross-sectional view of the rotational coupler of the endoscopic tool.

The endoscopic tool 100, as shown in FIGS. 1A-8B, may be configured to be inserted within an instrument channel of an endoscope. Examples of the endoscope can include a gastroscope, such as a colonoscope, a laryngoscope, or any other flexible endoscope. The endoscopic tool can include a flexible portion 102 that is shaped, sized and configured to be inserted within the instrument channel, while a remaining portion of the endoscopic tool 100 can be configured to remain outside the instrument channel of the endoscope. The flexile portion 102 can be shaped and sized to fit within the instrument channel and be configured to navigate through a tortuous path defined by the instrument channel while the endoscope is inserted within the patient. In the case of colonoscopes, the endoscope can form a series of bends of over at least 60 degrees and in some situations, over 90 degrees.

The endoscopic tool 100 can include a cutting assembly 110 configured to resect material at a site within a subject. In some implementations, the cutting assembly 110 can include an outer cannula and an inner cannula disposed within the outer cannula. The outer cannula can define an opening 112 through which material to be resected can enter the cutting assembly 110. In some implementations, the opening 112 is defines through a portion of the radial wall of the outer cannula. In some implementations, the opening may extend around only a portion of the radius of the outer cannula, for example, up to one third of the circumference of the radial wall. As the aspiration channel 190 extends between the aspiration port 192 and the opening 112, any suction applied at the aspiration port 192 causes a suction force to be exerted at the opening 112. The suction force causes material to be introduced into the opening of the outer cannula, which can then be cut by the inner cannula of the cutting assembly.

The inner cannula can include a cutting section that is configured to be positioned adjacent to the opening 112 such that material to be resected that enters the cutting assembly via the opening 112 can be resected by the cutting section of the inner cannula. The inner cannula may be hollow and an inner wall of the inner cannula may define a portion of an aspiration channel that may extend through the length of the endoscopic tool. A distal end of the inner cannula can include the cutting section while a proximal end of the inner cannula can be open such that material entering the distal end of the inner cannula via the cutting section can pass through the proximal end of the inner cannula. In some implementations, the distal end of the inner cannula can come into contact with an inner surface of a distal end of the outer cannula. In some implementations, this can allow the inner cannula to rotate relative to the outer cannula along a generally longitudinal axis, providing more stability to the inner cannula while the inner cannula is rotating. In some implementations, the size of the opening can dictate the size of the materials being cut or resected by the inner cannula. As such, the size of the opening may be determined based in part on the size of the aspiration channel defined by the inner circumference of the flexible torque coil.

The endoscopic instrument 100 can include a flexible torque coil 180 that is configured to couple to the proximal end of the inner cannula at a distal end of the flexible torque coil 180. The flexible torque coil can include a fine coil with multiple threads and multiple layers, which can transmit the rotation of one end of the flexible torque coil to an opposite end of the flexible torque coil. Each of the layer of thread of the flexible torque coil can be wound in a direction opposite to a direction in which each of the layer of thread adjacent to the layer of thread is wound. In some implementations, the flexible torque coil can include a first layer of thread wound in a clockwise direction, a second layer of thread wound in a counter-clockwise direction and a third layer of thread wound in a clockwise direction. In some implementations, the first layer of thread is separated from the third layer of thread by the second layer of thread. In some implementations, each of the layers of thread can include one or more threads. In some implementations, the layers of thread can be made from different materials or have different characteristics, such as thickness, length, among others.

The flexibility of the torque coil 180 allows the coil to maintain performance even in sections of the torque coil 180 that are bent. Examples of the flexible torque coil 180 include torque coils made by ASAHI INTECC USA, INC located in Santa Ana, Calif., USA. In some implementations, the flexible torque coil 180 can be surrounded by a sheath or lining to avoid frictional contact between the outer surface of the flexible torque coil 180 and other surfaces. In some implementations, the flexible torque coil 180 can be coated with Polytetrafluoroethylene (PFTE) to reduce frictional contact between the outer surface of the flexible torque coil 180 and other surfaces. The flexible torque coil 180 can be sized, shaped or configured to have an outer diameter that is smaller than the diameter of the instrument channel of the endoscope in which the endoscopic tool is to be inserted. For example, in some implementations, the outer diameter of the flexible torque coil can be within the range of 1-4 millimeters. The length of the flexible torque coil can be sized to exceed the length of the endoscope. In some implementations, the inner wall of the flexible torque coil 180 can be configured to define another portion of the aspiration channel that is fluidly coupled to the portion of the aspiration channel defined by the inner wall of the inner cannula of the cutting assembly 110. A proximal end of the flexible torque coil 180 can be coupled to a proximal connector assembly 170, details of which are provided below.

The endoscopic instrument 100 can include a flexible outer tubing 186 that can be coupled to the proximal end of the outer cannula. In some implementations, a distal end of the flexible outer tubing 186 can be coupled to the proximal end of the outer cannula using a coupling component. In some implementations, the outer cannula can be configured to rotate responsive to rotating the flexible outer tubing. In some implementations, the flexible outer tubing 186 can be a hollow, braided tubing that has an outer diameter that is smaller than the instrument channel of the endoscope in which the endoscopic instrument 100 is to be inserted. In some implementations, the length of the flexible outer tubing 186 can be sized to exceed the length of the endoscope. The flexible outer tubing 186 can define a bore through which a portion of the flexible outer tubing 186 extends. The flexible outer tubing 186 can include braids, threads, or other features that facilitate the rotation of the flexible outer tubing 186 relative to the flexible torque coil, which is partially disposed within the flexible outer tubing 186.

The endoscopic instrument 100 can include a rotational coupler 130 configured to be coupled to a proximal end of the flexible outer tubing 186. The rotational coupler 130 may be configured to allow an operator of the endoscopic tool to rotate the flexible outer tubing 186 via a rotational tab 132 coupled to or being an integral part of the rotational coupler 130. By rotating the rotational tab 132, the operator can rotate the flexible outer tubing and the outer cannula along a longitudinal axis of the endoscope and relative to the endoscope and the inner cannula of the cutting assembly 110. In some implementations, the operator may want to rotate the outer cannula while the endoscopic instrument is inserted within the endoscope while the endoscope is within the patient. The operator may desire to rotate the outer cannula to position the opening of the outer cannula to a position where the portion of the radial wall of the outer cannula within which the opening is defined may aligned with the camera of the endoscope such that the operator can view the material entering the endoscopic instrument for resection via the opening. This is possible in part because the opening is defined along a radial wall extending on a side of the outer cannula as opposed to an opening formed on the axial wall of the outer cannula.

In some implementations, a proximal end 134 of the rotational coupler 130 can be coupled to a lavage connector 140. In some implementations, the rotational coupler 130 can be a rotating luer component that allows a distal end 136 of the rotational coupler 130 rotate relative to the proximal end 134 of the rotational coupler 130. In this way, when the flexible outer tubing 186 is rotated, the component to which the proximal end of the rotational coupler 130 is coupled, is not caused to rotate. In some implementations, the proximal end 134 of the rotational coupler 130 can be coupled to an outer tubular member 144 configured to couple the proximal end 134 of the rotational coupler 130 to the lavage connector 140. The rotational coupler 130 can define a bore along a central portion of the rotational coupler 130 through which a portion of the flexible torque coil 180 extends. In some implementations, the rotational coupler 130 can be a male to male rotating luer connector. In some implementations, the rotational coupler can be configured to handle pressures up to 1200 psi.

The lavage connector 140 can be configured to introduce irrigation fluid into the endoscopic tool 100. The lavage connector 140 includes a lavage port 142 configured to engage with an irrigation source, such as a water container. In some implementations, the lavage connector 140 can be a Y port used in fluid delivery systems that complies with medical device industry standards and is sized to couple to the flexible outer tubing 186 or the outer tubular member 144 that serves to couple a distal end 148 of the lavage connector 140 to the proximal end 134 of the rotational coupler 130. In some implementations, the lavage connector can define a hollow channel between the proximal end 146 and the distal end 148 of the lavage connector 140 that is sized to allow the flexible torque coil 180 to pass through the hollow channel defined through the lavage connector 140.

As described above, the proximal connector assembly 170 is configured to be coupled to a proximal end of the flexible torque coil 180. The proximal connector assembly 170 can be configured to engage with the drive assembly 150 that is configured to provide torque to the inner cannula via the proximal connector assembly 170 and the flexible torque coil 180. The proximal connector assembly 170 can further define a portion of the aspiration channel and be configured to fluidly couple the aspiration channel to a vacuum source to facilitate the removal of material entering the aspiration channel. In some implementations, a proximal end of the proximal connector assembly 170 can include an aspiration port 192 through which the material that enters the endoscopic tool 100 can be withdrawn from the endoscopic tool 100.

In some implementations, the endoscopic tool 100 can be configured to be driven by the drive assembly 150. The drive assembly 150 is configured to provide rotational energy from an energy source to the endoscopic tool 100. The drive assembly 150 can include a housing 160 that may house a first beveled gear 154 and a second beveled gear 156 that are positioned such that the rotation of the first beveled gear 154 causes a rotation of the second beveled gear 156. The second beveled gear 156 can be coupled to a drive receptacle that is sized and shaped to receive and engage with the proximal connector assembly 170 of the endoscopic tool 100. In some implementations, the first beveled gear 154 can be coupled to a motor (not shown) or other rotational source via a rotational input shaft 152.

The proximal connector assembly 170 can include a hollow drive shaft 172, a coupler 176 through which the hollow drive shaft 172 passes and a tensioning spring 174 coupled to the hollow drive shaft 172. A distal end of the drive shaft 172 can be coupled to the proximal end of the flexible torque coil 180. In some implementations, the drive shaft 172 and the flexible torque coil 180 can be permanently coupled to one another. In some implementations, the drive shaft 172 and flexible torque coil 180 can be coupled using a coupler, a press fit, a weld, such as a butt weld, or any other attachment means that allows the flexible torque coil 180 to rotate when the drive shaft 172 rotates and to allow material passing through the flexible torque coil 180 to flow through the drive shaft 172. A proximal end of the drive shaft 172 can define the aspiration port 192. In some implementations, the aspiration port 192 can be configured to engage with a vacuum source causing material entering the opening 112 to flow through the aspiration channel 190 and out of the endoscopic tool through the aspiration port 192.

A coupler 176, such as a hex-shaped coupler, can be configured to couple with the hollow drive shaft. In some implementations, the hex-shaped coupler is a part of the hollow drive shaft. The coupler 176 can include an outer wall that is configured to engage with an inner wall of a drive receptacle 158. The drive receptacle 158 is coupled to the second beveled gear 156 and is configured to rotate when the second beveled gear 156 rotates. In some implementations, the drive receptacle 158 can be a hollow cylindrical tube. In some implementations, a proximal end 159 of the drive receptacle 158 can include an opening defined by an inner wall of the proximal end of the drive receptacle 158 that has a diameter that smaller than the inner diameter of the remaining portion of the drive receptacle 158. In some implementations, the diameter of the opening through the proximal end 159 of the drive receptacle 158 can be large enough to receive the drift shaft 172 but small enough to prevent the tensioning spring 174 coupled to the drive shaft 172 from passing through the opening. In some implementations, the inner diameter of the remaining portion of the drive receptacle is sized to engage with the coupler 176.

The tensioning spring 174 can be biased in such a way that, during operation of the endoscopic tool 100, the tensioning spring 174 may prevent the drive shaft 172, the flexible torque coil 180 and the inner cannula from sliding towards the proximal end of the endoscopic tool 100. In some implementations, without the tensioning spring 174, the inner cannula may slide away from the distal end of the endoscopic tool 100. This may be due to a force applied by the material to be resected at the opening 112. In some implementations, the tensioning spring 174 provides a countering force that prevents the inner cannula from sliding away from the distal end when the inner cannula comes into contact with the material to be resected at the opening 112. In some implementations, the tensioning spring 174 can be configured to bias the distal end of the inner cannula to contact an inner wall of the distal end of the outer cannula. In some implementations, the tensioning spring 174 can be sized and biased such that the distal tip of the inner cannula can contact the inner distal wall of the outer cannula. This may limit any lateral or undesired movement generated due to whip at the distal end of the inner cannula caused by the rotation of the flexible torque coil.

The housing 160 can be configured to engage with an aspiration end cap 162 and a locking collar 164. In some implementations, the aspiration end cap 162 can be configured to allow a vacuum source to maintain a secure connection with the aspiration port 192 of the drive shaft 172. In some implementations, the aspiration end cap 162 can be configured to allow the drive shaft 172 to rotate while maintaining a secure connection between the vacuum source and the aspiration port 192 of the drive shaft 172. In some implementations, the aspiration end cap 162 can be configured to be secured to a portion of the housing 160 in such a way that the aspiration port of the drive shaft 172 is accessible via an opening of the aspiration end cap 162. In some implementations, the vacuum source can be coupled to the end cap 162 such that the vacuum source does not rotate along with the proximal end of the drive shaft 172. In some implementations, one or more bearings or bushings can be used to allow facilitate a fluid connection between the aspiration port 192 of the drive shaft 172 and the vacuum source without causing the vacuum source to rotate with the drive shaft 172.

The locking collar 164 can be configured to secure the lavage connector 140 to the proximal connector assembly 170. In some implementations, the locking collar 164 can be configured to secure a proximal end 146 of the lavage connector 140 to the housing 160 of the drive assembly 150. The locking collar 164 can further be configured to prevent the proximal connector assembly 170 from disengaging with the drive receptacle 158 and moving towards the distal end of the endoscopic tool 100. In some implementations, the locking collar 164 can be configured to secure a lining 182 within which the flexible torque coil 180 is disposed to the flexible torque coil 180, the drive shaft 172 or the housing 160. In some implementations, the lining 182 can serve as a heat shrink to reduce the dissipation of heat generated in the flexible torque coil to other components of the endoscopic tool. In some implementations, the outer wall of the lining 182 can define a portion of the irrigation channel, while the inner wall of the lining 182 can serve to prevent any material passing through the aspiration channel from escaping through the walls of the flexible torque coil. In some implementations, the lining 182 can also prevent the irrigation fluid passing through the irrigation channel to flow into the aspiration channel 190 through the walls of the flexible torque coil 180.

The distal end 148 of the lavage connector 140 can be configured to engage with an inner wall of the outer tubing 144. In some implementations, the distal end 148 of the lavage connector 140 can be press fit into a proximal end of the outer tubing 144. In some implementations, a connector connecting the distal end 148 of the lavage connector 140 and the outer tubing can be used. The inner wall of the outer tubing 144 and the outer wall of the lining 182 can define a portion of the irrigation channel 196. The outer tubing 144 can extend from the distal end 148 of the lavage connector 140 to a proximal end 134 of the rotational coupler 130. The distal end of the outer tubing 144 can be configured to engage with the proximal end 134 of the rotational coupler 130.

In some implementations, the irrigation channel can extend from the irrigation entry port to the opening of the outer cannula. The irrigation channel can be defined by the inner wall of the outer tubular member, the rotational coupler, the inner wall of the outer tubing and the inner wall of outer cannula. In some implementations, the irrigation channel can also be defined by the outer wall of the inner cannula and the outer wall of the flexible torque coil 180. In some implementations, the endoscopic instrument 100 can also include the hollow lining 182 that is sized to fit around the flexible torque coil 180. In some implementations, the hollow lining 182 can serve as a barrier between the irrigation channel 196 and the aspiration channel 190. In some implementations, the hollow lining 182 can prevent air or other fluids to seep through the threads of the flexible torque coil 180. In addition, the hollow lining can allow the aspiration channel to maintain a suction force throughout the length of the aspiration channel by preventing air to escape or enter through the threads of the flexible torque coil 180.

As described above, the cutting assembly 110 includes the outer cannula. The braided tubing 186 is coupled to the outer cannula such that rotating the rotational tab 132 of the rotational coupler 130 results in rotating the outer cannula. The outer cannula includes the opening 112 at a distal end of the outer cannula. The opening is defined within a portion of the radial wall of the outer cannula and may only extend around a portion of the radius of the outer cannula. As the aspiration channel 190 extends between the aspiration port 192 and the opening 112, any suction applied at the aspiration port 192 causes a suction force to be exerted at the opening 112. The suction force causes material to be introduced into the opening of the outer cannula, which can then be cut by the inner cannula of the cutting assembly. In some implementations, the aspirated material can be collected in a collection cartridge. In some implementations, the collection cartridge can be fluidly coupled to the proximal end of the aspiration channel.

The inner cannula is disposed within the outer cannula and configured to resect any material that is sucked into or otherwise enters the opening 112 due to the suction force in the aspiration channel 190. The inner cannula can cut, resect, excise, debride or shave the material at the opening 112 based in part on the interaction between the cutting surface and the wall of the outer cannula that defines the opening. In some implementations, the rotational movement of the cutting surface relative to the opening 112 can cause the material to be cut, resected, excised, or shaved. The flexible torque coil is coupled to the inner cannula and causes the inner cannula to rotate along the longitudinal axis of the inner cannula. As the outer cannula is coupled to the outer tubing and is not rotationally coupled to the inner cannula or flexible torque coil, the inner cannula rotates relative to the outer cannula. A gap between an outer wall of the inner cannula and the inner wall of the outer cannula defines a portion of the irrigation channel through which irrigation fluid can flow from the lavage connector 140 through the irrigation channel portion defined in part by the outer tubing 144, the rotational coupler 130, and the flexible outer tubing 186 towards the cutting surface of the inner cannula. The inner cannula may define a portion of the aspiration channel through which excised or resected material and the irrigation fluid can flow from the cutting surface of the inner cannula towards the aspiration port 192.

The length of the cutting assembly 110 may be sized to allow the endoscopic instrument 100 to traverse through the length of the endoscope while the endoscope is inserted inside a patient. In some implementations, the endoscope may be disposed within the patient and the endoscope may include bends that exceed 60 degrees. As such, the length of the cutting assembly 110 may not exceed a few centimeters. In some implementations, the length of the cutting assembly 110 may be less than 1% of the length of the endoscopic tool 100, or the length of the flexible portion of the endoscope within which the endoscopic tool can be inserted. As described above, tissue sensing capabilities can be implemented with the cutting assembly serving as a portion of the tissue sensor.

It should be appreciated that one or more seals, bearings, and other components may be used. Seals may be used to maintain pressure, prevent fluid leaks, or to securely engage components to one another. In some implementations, bearings may be used to allow components to rotate relative to one another without adversely affecting the components or the performance of the endoscopic tool.

FIG. 6 shows a cross-sectional view of the endoscopic tool and the portion of the drive assembly across the section B-B. As shown in FIG. 6, the second beveled gear 156 may be configured to engage with the drive receptacle 158 of the drive assembly 150. The proximal connector 170 of the endoscopic tool 100, which includes the coupler 176 and the drive shaft 172, can be inserted disposed within the drive receptacle 158. The outer wall of the coupler 176 is sized to engage with the inner wall of the drive receptacle 158 such that when the drive receptacle 158 rotates, the coupler 176 also rotates. Because the coupler 176 is coupled to the drive shaft 172, the drive shaft 172 may also rotate when the drive receptacle 158 rotates. The inner wall of the drive shaft defines a portion of the aspiration channel 190.

FIG. 7 shows an enlarged cross-sectional view of the rotational coupler section of the endoscopic tool. FIG. 8A and FIG. 8B show a top view and a cross-sectional view of the rotational coupler of the endoscopic tool.

As shown in FIGS. 7-8B, the outer tubing 144 is configured to engage with the rotational coupler 130. The outer tubing 144 surrounds the lining 182, which in turn surrounds the flexible torque coil 180. The inner wall of the flexible torque coil 180 may define a portion of the aspiration channel 190. The space between the inner wall of the outer tubing 144 and the outer wall or surface of the lining 182 defines a portion of the irrigation channel. The tab 132 can be configured to be rotated by an operator of the endoscopic tool. In some implementations, the operator can rotate the tab 132 while the endoscopic tool is inserted within the instrument channel of the endoscope and cause the outer cannula to rotate relative to the inner cannula and the endoscope. In this way, the operator can position the opening defined through the outer cannula by rotating the outer cannula to a desired position. In some implementations, by providing a mechanism through which the outer cannula can be rotated relative to the endoscope, an operator does not have to be concerned about the position of the opening when the endoscopic tool is inserted within the instrument channel of the endoscope as the operator may be able to adjust the position of the opening by causing the outer cannula to rotate while the endoscopic tool is inserted within the endoscope.

Figure 9:
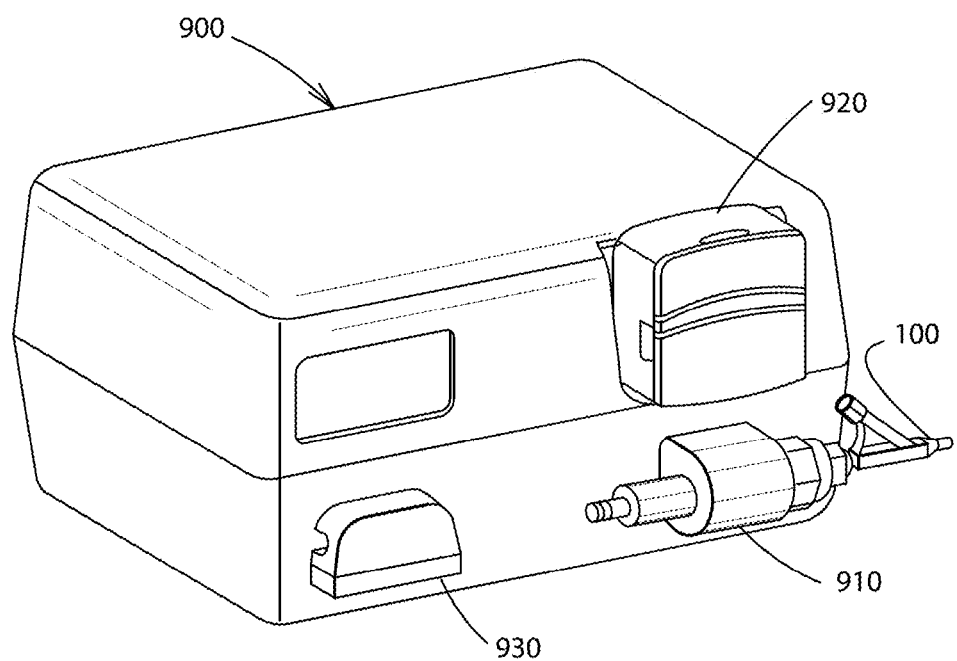
FIG. 9 is a perspective view of a portion of the endoscopic tool inserted for operation within a drive assembly according to embodiments of the present disclosure.
Figure 10:
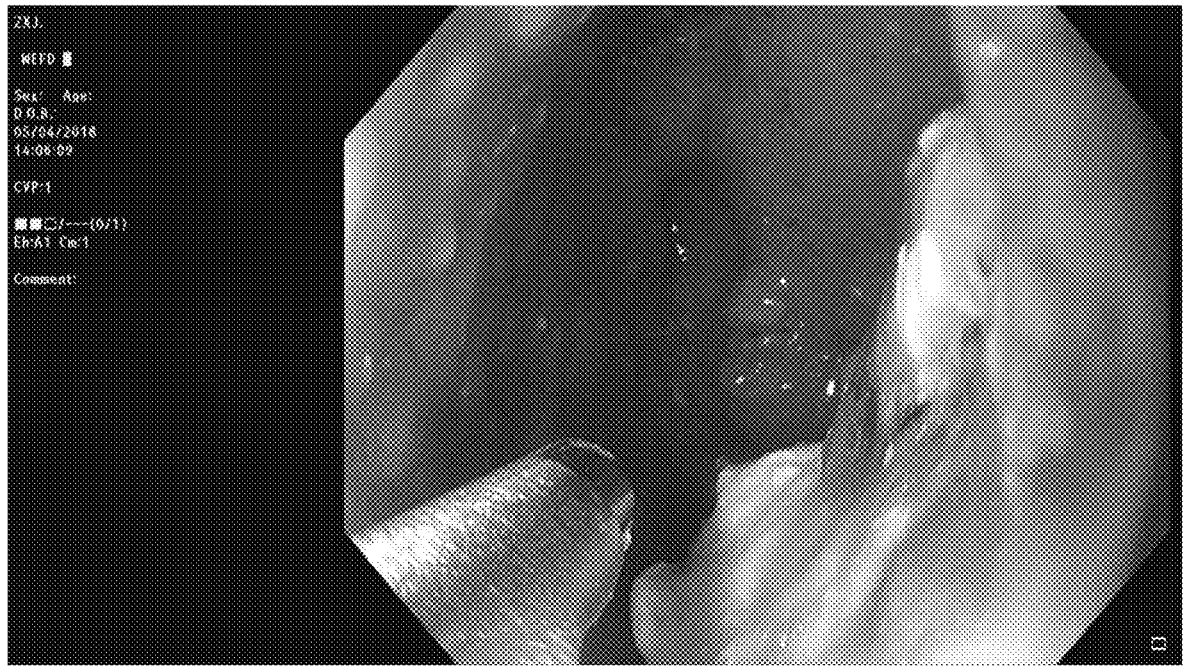
FIGS. 10-20 illustrate images of an endoscopic pancreatic procedure.
Figure 11:
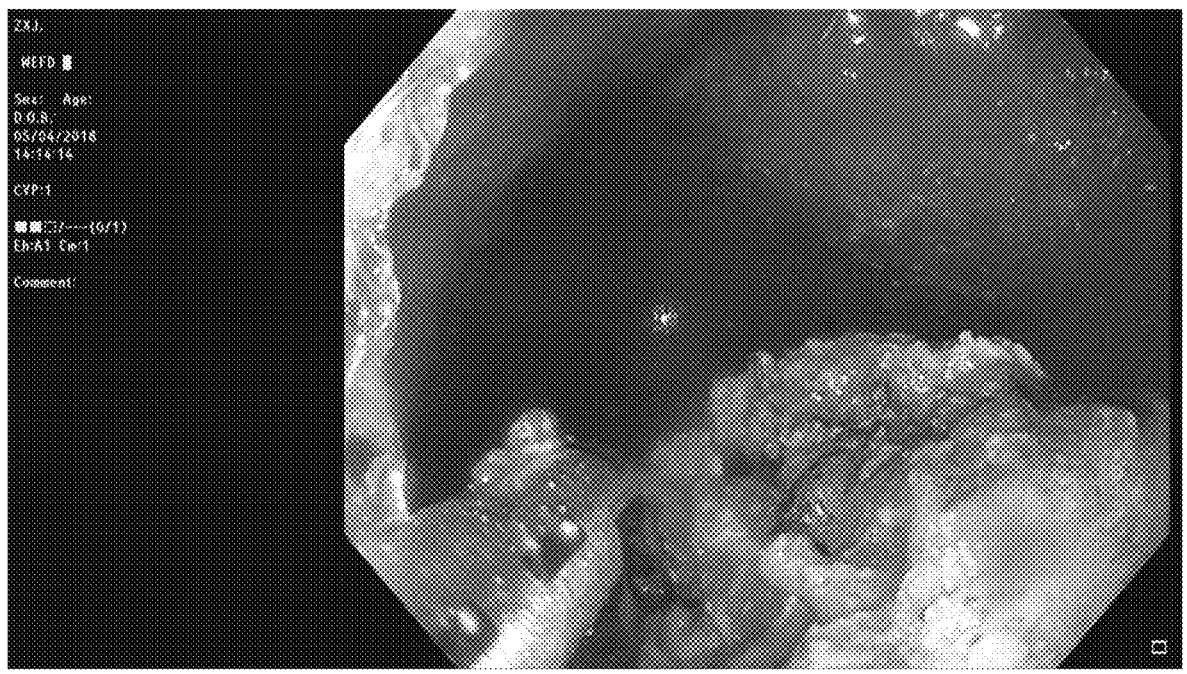
Figure 12:
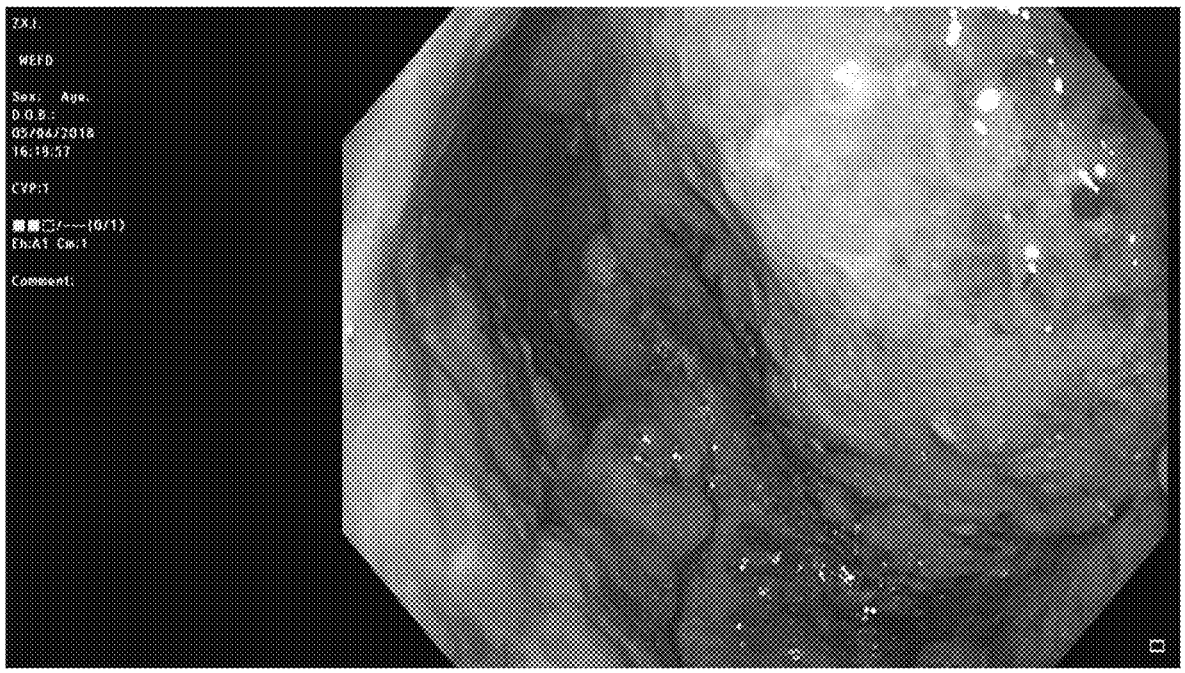
Figure 13:
Figure 14:
Figure 15:
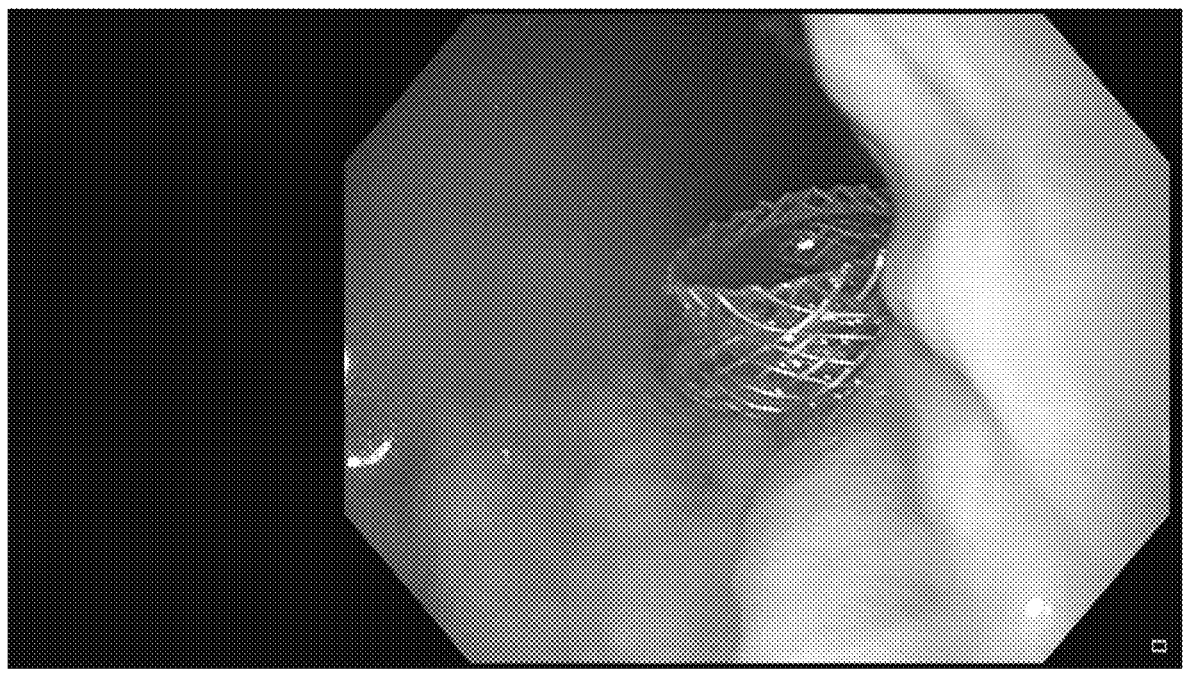
Figure 16:
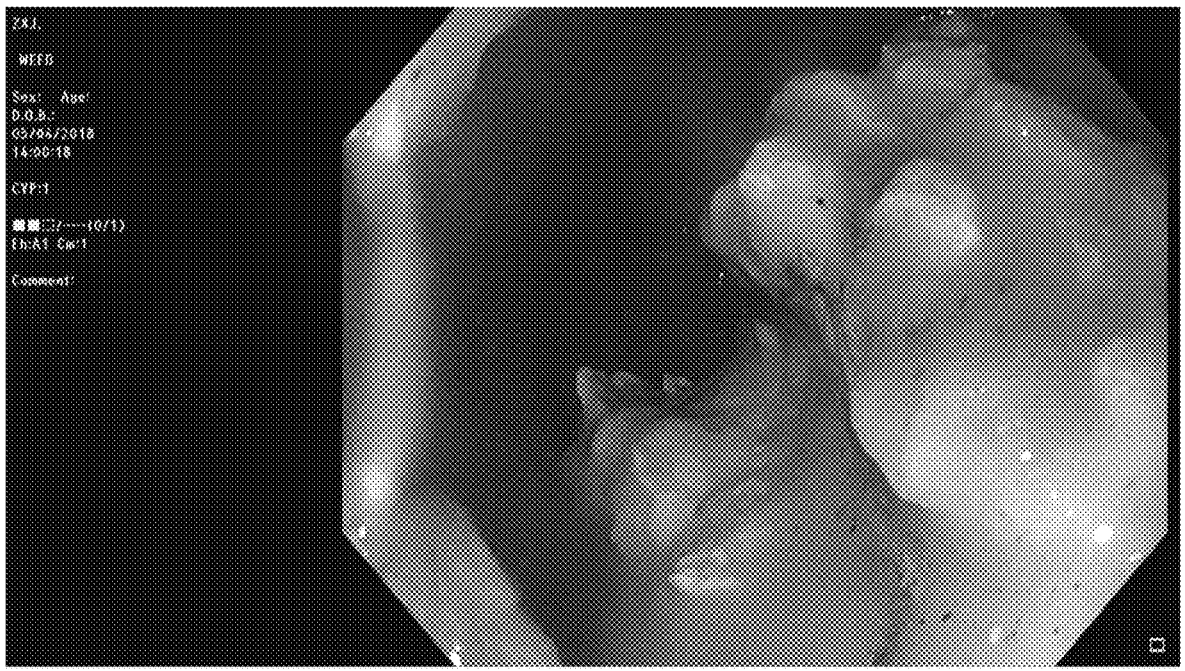
Figure 17:
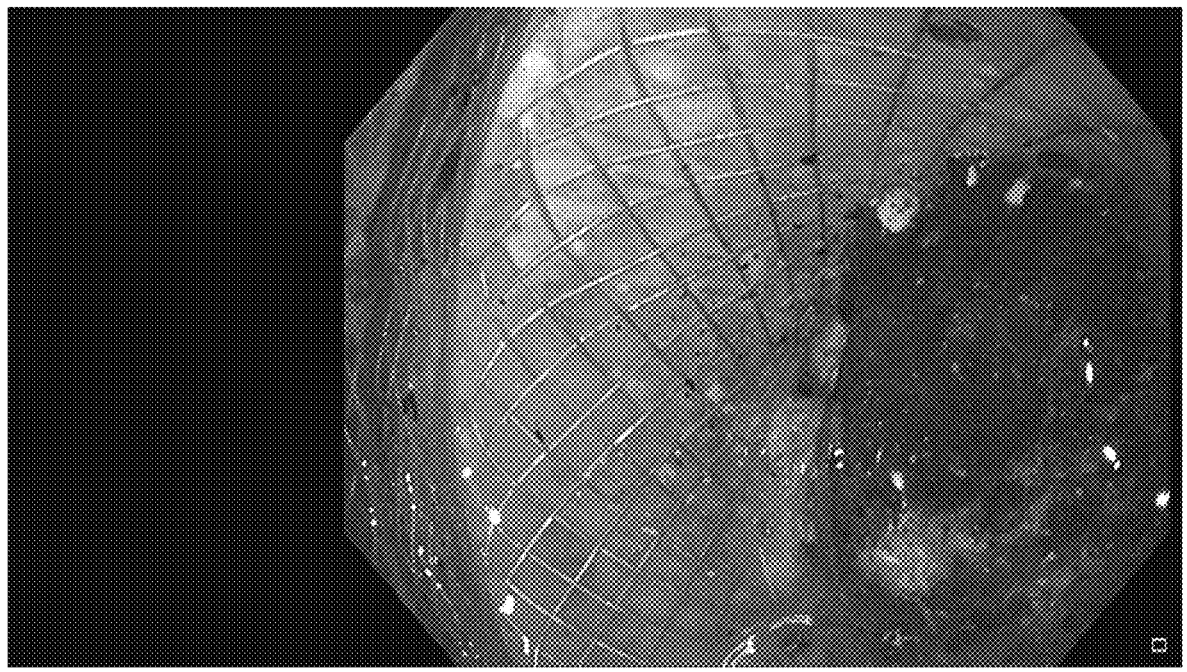
Figure 18:
Figure 19:
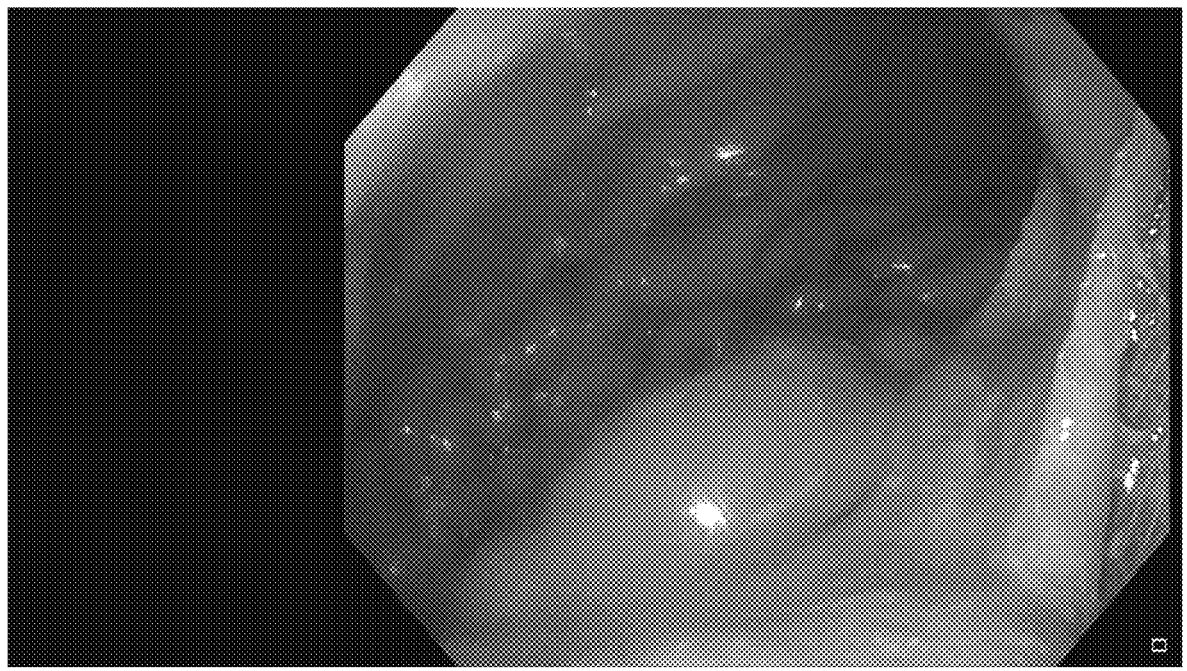
Figure 20:
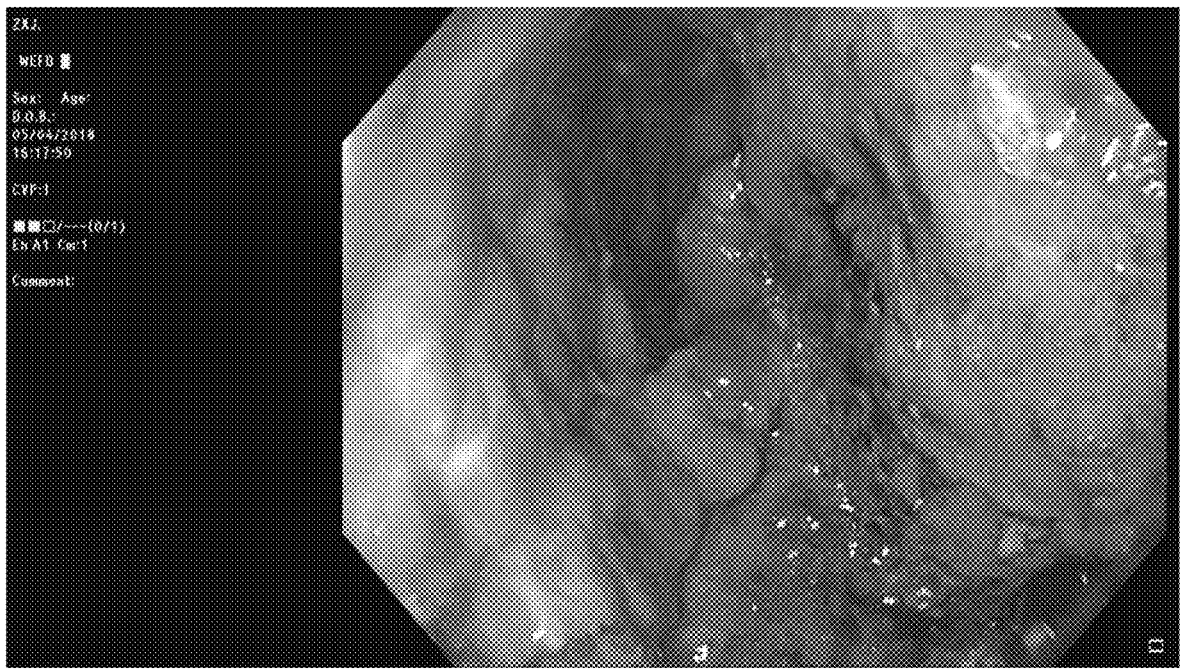

FIG. 9 is a perspective view of a portion of the endoscopic tool inserted for operation within a drive assembly. The drive assembly 900 includes a drive interface 910 configured to receive the proximal connector 170 of the endoscopic tool 100. The proximal connector 170 can engage with the drive receptacle of the drive interface 910 to translate rotational energy generated by the drive assembly 900 to the cutting assembly of the endoscopic tool 100. The drive assembly 900 may include a pump 920 or other fluid displacement device to control the flow of irrigation fluid into the lavage port 142 of the endoscopic tool 100. In some implementations, the pump 920 can be a peristaltic pump. In some implementations, the pump can be any positive displacement fluid pump. In some implementations, a valve between the pump 920 and the lavage port 142 can be placed to control an amount of irrigation fluid entering the endoscopic tool. In some implementations, the speed at which the pump 920 operates can dictate the rate at which irrigation fluid enters the endoscopic tool. The drive assembly can also include a pinch valve 930. In some implementations, the pinch valve can be configured to control the application of a suction force applied to the aspiration channel.

In some implementations, an actuator, such as a control switch can be used to actuate the drive assembly 900. In some implementations, the actuator can be a foot pedal, a hand switch, or any other actuation means for controlling the drive assembly 900. In some implementations, the actuator can be coupled to the drive means, such as the pump 920 such that when the actuator is actuated, the pump 920 begins to rotate, generating torque, which is translated to the proximal connector of the endoscopic tool via the drive interface 910. The torque applied to the proximal connector can be translated via the flexible torque coil to the inner cannula, thereby causing the inner cannula to rotate relative to the outer cannula. In some implementations, the actuator can be coupled to a pinch valve, such as the pinch valve 930 to control the amount of suction applied to the aspiration channel. In some implementations, the actuator can be configured to actuate both the drive means and the pinch valve simultaneously, such that the inner cannula is rotating while suction is applied through the aspiration channel. In some implementations, the actuator can also be coupled to an irrigation control switch or valve that controls the flow of irrigation fluid into the endoscopic tool via the irrigation entry port 142. In some implementations, the actuator can be configured to actuate the drive means, the pinch valve for aspiration and the irrigation control switch for irrigation simultaneously, such that the inner cannula is rotating while suction is applied through the aspiration channel and irrigation fluid is supplied to the endoscopic tool.

In some implementations, a separate irrigation control switch can be configured to control the flow of irrigation fluid through the irrigation channel of the endoscopic tool. An operator can control the volume of irrigation fluid provided to the irrigation channel via the irrigation control switch.

The drive assembly configuration shown in FIGS. 1A-9 is one example configuration of a drive assembly. It should be appreciated that the endoscopic tool 100 can be configured to be driven by other drive assembly configurations. In some implementations, the proximal connector portion of the endoscopic tool 100 can be modified to engage with other drive assembly configurations. In some implementations, the endoscopic tool 400 can be configured to be packaged as one or more different components that can be assembled prior to inserting the endoscopic tool within the instrument channel of the endoscope. In some implementations, the proximal connector of the endoscopic tool 100 can be assembled together by an operator of the endoscopic tool after one or more components of the endoscopic tool are caused to engage with components of the drive assembly.

It should be appreciated that the outer diameter of the endoscopic instrument may be sized to be inserted within the instrument channel of an endoscope while the endoscope is inserted within a patient. In addition, the endoscopic instrument may be sized to be large enough that the endoscopic tool comes into contact with the inner walls of the instrument channel at various portions of the instrument channel to maintain stability of the endoscopic instrument. If the outer diameter of the endoscopic instrument is much smaller than the inner diameter of the instrument channel, there may be a large amount of space between the endoscopic instrument and the inner wall of the instrument channel, which may allow the endoscopic instrument to move, vibrate or otherwise experience some instability during operation.

B. Systems and Methods for Removing Materials from the Pancreas Using an Endoscopic Surgical Tool Pancreatic procedures may be performed to address necrotic tissue that can result in fluid collections in the pancreas or external to the pancreas, such as due to walled-off pancreatic necrosis. Around twenty percent of subjects with acute pancreatitis develop necrotizing pancreatitis, with about a third of them progressing to infected necrosis. Infected necrosis may not respond to conservative treatment, such that invasive or interventional treatment may be necessary. Some endoscopic procedures have been used to treat these conditions; however, these procedures may rely on devices designed for other indications, such as lithotripsy baskets, retrieval nets, polypectomy snares, and grasping forceps, which may be able to grasp and hold material, but lack a sufficient grasp on the necrotic tissue. This can make the procedures cumbersome, time consuming, and limited in effectiveness, often requiring numerous cycles of tissue resection and suction in order to complete the treatment (e.g., only small amounts of necrosis being pulled out per pass).

In accordance with various aspects of the present disclosure, subjects with infected walled-off pancreatic necrosis can be endoscopically treated using an endoscopic tool. Procedures can be performed under conscious or propofol sedation. The endoscopic tool can be coupled with an endoscope, such as to be advanced through an instrument channel or accessory channel of the endoscope, or coupled to the endoscope by a sheath. A cutting assembly of the endoscopic tool can be driven (e.g., rotated or reciprocated) to remove material such as infected tissue, which can be immediately removed by applying suction to an aspiration channel of the endoscopic tool. The cutting assembly can be used to remove material associated with fluid collections in the pancreas as well as external to the pancreas. The endoscopic tool can be guided into the stomach of the subject (e.g., in conjunction with the endoscope), and introduced to a site from which to remove the material through an opening, such as a cystgastrostomy generated using a stent, in a cavity wall of the stomach. For example, the stent may be used to create a fistula through which an interior of the pancreas can be accessed by the endoscopic tool.

In some embodiments of procedures performed in accordance with the present disclosure, the average procedure length was 46.5 minutes (range 32-80). To achieve complete removal of pancreatic necrosis the median number of required procedures was two per patient (range 1-7). No procedure-related adverse events occurred. Endoscopists agree on the ease of use and effective removal of necrotic tissue with the ENDOROTOR, rating both 8.3 on a 10-point scale. They are especially satisfied by the ability to manage the removal of necrotic tissue in a controlled way (8.6 on a 10-point scale).

The endoscopic tool can be used in the gastrointestinal tract for benign neoplastic or pre-malignant tissue removal by interventional gastroenterologists and GI surgeons. The endoscopic tool can perform both tissue dissection and resection with a single device through an endoscope's instrument biopsy channel. A motorized rotating cutting tool driven by an electronically controlled console can perform tissue resection. The system can automatically suction and cut between 1000 and 1750 times a minute, such that resected tissue can be immediately aspirated away from the resection site and collected onto a micron filter. Tissue collected on the filters can be used for pathological examination using standard methods. FIGS. 10-20 illustrate various operations associated with performing endoscopic procedures to address pancreatic necrosis.

Infected walled of necrosis (WON) is a complication of acute pancreatitis. Direct endoscopic intervention can remove the necrosis and improve patient recovery. Existing procedures employ the use of instruments not designed for the procedure such as endoscopic snares/jumbo forceps to break up necrosis followed by endoscopic retrieval baskets to remove necrotic debris. The ability of the endoscopic tool to resect tissue may provide faster rates of removal and less endoscopic procedures in this patient population.

Acute pancreatitis can be defined by sudden inflammation of the pancreatic gland, which functions to make insulin and enzymes for the digestion of food. While the cause of acute pancreatitis can vary greatly among patients, severe cases can lead to development of life threatening complications, such as walled-off pancreatic necrosis (WOPN). Pancreatic necrosis can be defined when more than 30% of the gland is affected by necrosis with 20% of patients requiring severe clinical course. Of the 20%, one third (33.3%) of cases may progress to infected necrosis with patient mortality ranging from 15-30%. Should acute necrotic collections continue to progress, results may lead to the development of WOPN after 4 weeks time.

The endoscopic tool can enable safe and effective removal of pancreatic necrosis—due to its automated mechanical characteristics, which incorporate rotational cutting and suction for tissue removal in one inclusive device. In some embodiments, the endoscopic tool is the ENDOROTOR manufactured by Interscope, Inc. of Whitinsville, Mass. The procedure can utilize the endoscopic tool in necrosectomy procedures to resect or remove WOPN accessed via trans gastric fistulas created by luminal apposing metal stents (LAMS) and plastic pig tail stents. While the endoscopic tool is used to resect necrotic tissue in the cavity perforation may not present a risk with no interaction with wall of pancreas and further there was no evidence of bleeding in the series. The endoscopic tool can demonstrate complete removal of pancreatic necrosis through various anastomosing stents with no incidences of perforation or bleeding.

During an initial endoscopy, endoscopic ultrasound (EUS) guided transgastric drainage can be performed by creating a fistula from the stomach to directly access the adjacent WOPN site for collection. Pigtail plastic stents and a nasocystic flushing catheter, or Luminal Apposing Metal Stents (LAMS), can be positioned.

Subjects can be treated approximately twenty-four hours after the initial drainage procedure; a second endoscopy can be during which the fistula was dilated with a CRE™ Balloon Dilator to 18 mm and can be followed by initial attempts at necrosectomy with conventional instruments. Upon execution of necrosectomy with conventional instruments, the amount of necrotic tissue that could be removed was insufficient and clinical improvement was not observed. Necrosectomy performed with the endoscopic tool technique can result in complete removal of all necrotic tissue and in two sessions with no adverse events; a subject maybe discharged 7 days after admission.

On average, two (2) sessions may be required to remove the pancreatic necrosis. Reduction of required procedures to achieve favorable removal of necrotic pancreatic tissue can result in patient discharges within a few weeks versus an average of 6.2 sessions and almost twelve (12) weeks using conventional instrumentation.

Figure 21:
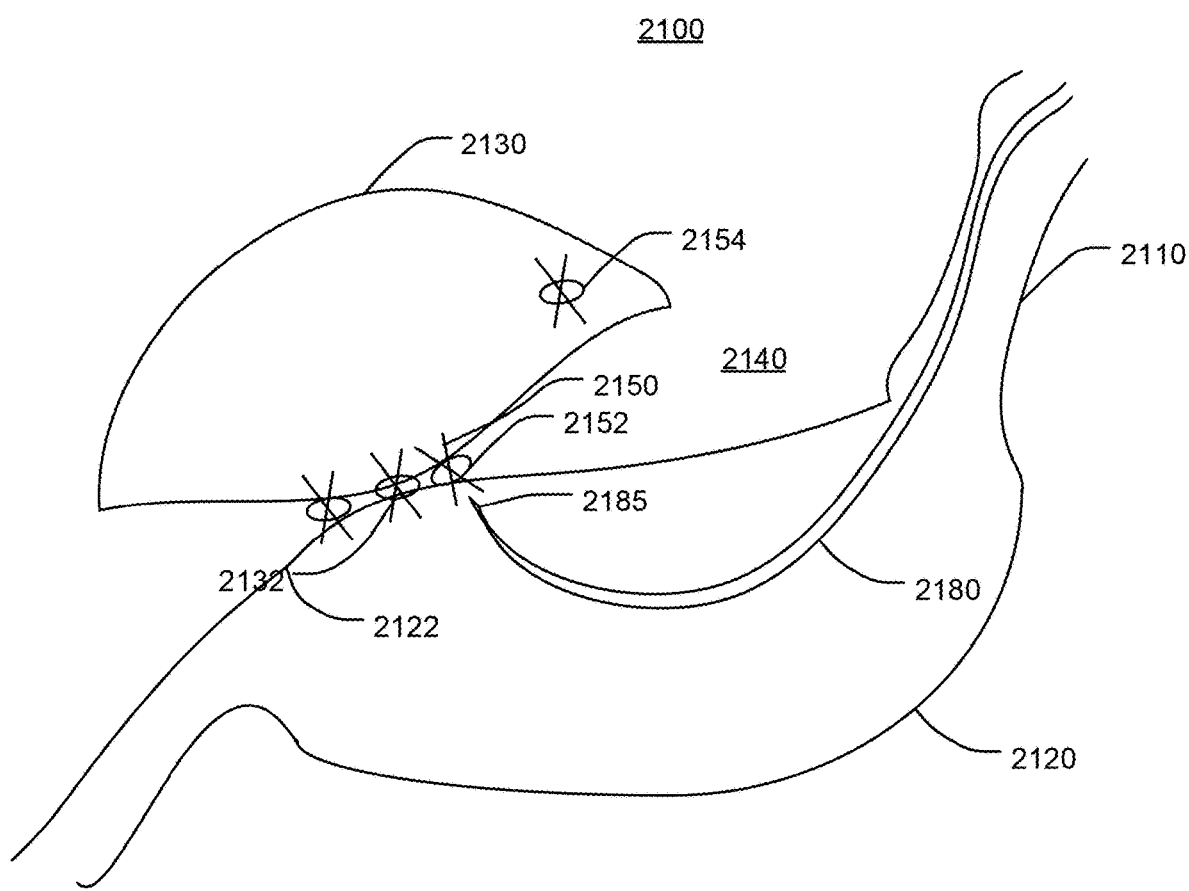
FIG. 21 is a schematic diagram of a torso region of a subject at which an endoscopic pancreatic procedure can be performed.

Referring now to FIG. 21, a schematic diagram of a torso region 2100 of a subject is shown according to an embodiment of the present disclosure. The torso region 2100 can include an esophagus 2110, a stomach 2120, a pancreas 2130, and a body cavity 2140 defined by space in the torso region 2100 between tissues/organs.

The pancreas 2130 may be in a state of pancreatitis, such as a state of necrosis (e.g., WOPN). An endoscopic procedure can be performed as described herein to treat the pancreas 2130. For example, an endoscopic tool 2180 (e.g., the ENDOROTOR) can be used to resect material from the pancreas 2130, such as inflamed and/or necrotic material (e.g., acute necrotic collections). The endoscopic tool 2180 can be used to resect material inside or external to the pancreas. The endoscopic tool 2180 includes a distal end 2182 that includes an inner cannula and outer cannula that can be rotated relative to one another to cut material, along with suction for withdrawing the cut material through the endoscopic tool 2180. Using the automated mechanical characteristics of the endoscopic tool, which incorporate rotational cutting and suction for tissue removal in one inclusive device, the treatment can be performed more effectively than existing procedures that rely on snares or forceps for resect and endoscopic baskets for retrieval. The endoscopic tool 2180 can have a diameter greater than or equal to 3 mm and less than or equal to 7 mm (e.g., 3.1 mm); for example, as the diameter of the endoscopic tool 2180 increases, suction of material can be facilitated. The inner cannula can be rotated at a rotation rate greater than or equal to 700 revolutions per minute (RPM) and less than or equal to 2000 RPM (e.g., at a predetermined rate, such as 1000 RPM or 1700 RPM), which can enable the endoscopic tool 2180 to remove material more efficiently than in existing procedures, such as by chopping the necrotic tissue into small pieces. Suction can be applied at a vacuum pressure greater than or equal to 200 mmHg and less than or equal to 750 mmHg (e.g., 620 mmHg) to remove the material through the aspiration channel.

A plurality of cystgastrostomies, such as fistulas 2150, can be generated to enable access for the endoscopic tool 2180 out of the stomach 2120 and into the pancreas 2130. In some embodiments, a plurality of stents 2152 are used to generate respective fistulas 2150. The stents 2152 can include at least one of luminal apposing metal stents (LAMS), metal stents (e.g., fully covered metal stents), or plastic pig tail stents. As shown in FIG. 21, the stents 2152 are used to generate respective fistulas 2150 enabling access from the stomach 2120 to the pancreas 2130 by generating a channel through an opening in a stomach wall 2122 of the stomach and an opening in a pancreas wall 2132 of the pancreas 2130. One or more fistulas 2154 may also be generated remote from the stomach wall 2122, to enable access into the pancreas 2130 via the body cavity 2140. One or more fistulas 2154 may also be generated on the stomach wall 2122 to enable access to infected tissue outside of the pancreas 2130.

The endoscopic tool 2180 can be introduced into the pancreas 2130 via one or more of the fistulas 2152, 2154. For example, the endoscopic tool 2180 can be introduced through the esophagus 2110, into the stomach 2120, and then through one or more fistulas 2152 into the pancreas 2130. The endoscopic tool 2180 can also be introduced into the body cavity 2140 separately from the esophagus 2110 or other gastrointestinal pathways, and then through one or more fistulas 2154 into the pancreas 2130. The endoscopic tool 2180 can be introduced through an instrument channel or accessory channel of an endoscope (which may be external to the endoscope), or can be introduced externally to the endoscope, such as by using a sheath that couples the endoscopic tool 2180 and the endoscope (e.g., sheath 2310 described with reference to FIG. 23).

When positioned adjacent to a site in the subject from which to remove material, such as a site in the pancreas 2130, the endoscopic tool 2180 can be actuated to cut and remove material from the pancreas 2130, including inflamed or necrotic material (see FIGS. 10-20). For example, an image capture device of the endoscopic tool 2180 can be used to guide the endoscopic tool 2180 towards a material, the distal end 2185 can be positioned adjacent to the material, and the endoscopic tool 2180 can be actuated to cut the material (e.g., by rotating the inner cannula relative to the outer cannula). Suction can be applied via the distal end 2185 to remove the cut material.

In some embodiments, the distal end 2185 is positioned to be tangent or substantially tangent to a tissue plane of the material to be removed. For example, the distal end 2185 can be positioned such that the cutting window of the cutting assembly is rotated to be facing the material with near or direct contact of the inner cannula (e.g., the distal end 2185 is within a threshold distance of the tissue plane less than or equal to ten millimeters), which has been found to improve the ability of the endoscopic tool 2180 to break up the material for suction through the aspiration channel (e.g., vacuum alone may not be sufficient to remove the material). In some embodiments, the cutting window is adjusted to be within a threshold angle of tangent to the tissue plane. The threshold angle can be fifteen degrees. The threshold angle can be ten degrees. The threshold angle can be five degrees. The cutting window can be adjusted so that a rotation or reciprocation axis of the inner cannula is parallel to the tissue plane where the inner cannula contacts the tissue plane within the threshold angle. In some embodiments, the cutting window is positioned so that the tissue plane is between the cavity wall and the cutting window (e.g., to trap the necrotic tissue between the cavity wall and the cutter opening), which can facilitate tissue removal and subsequent suction.

Figure 22:
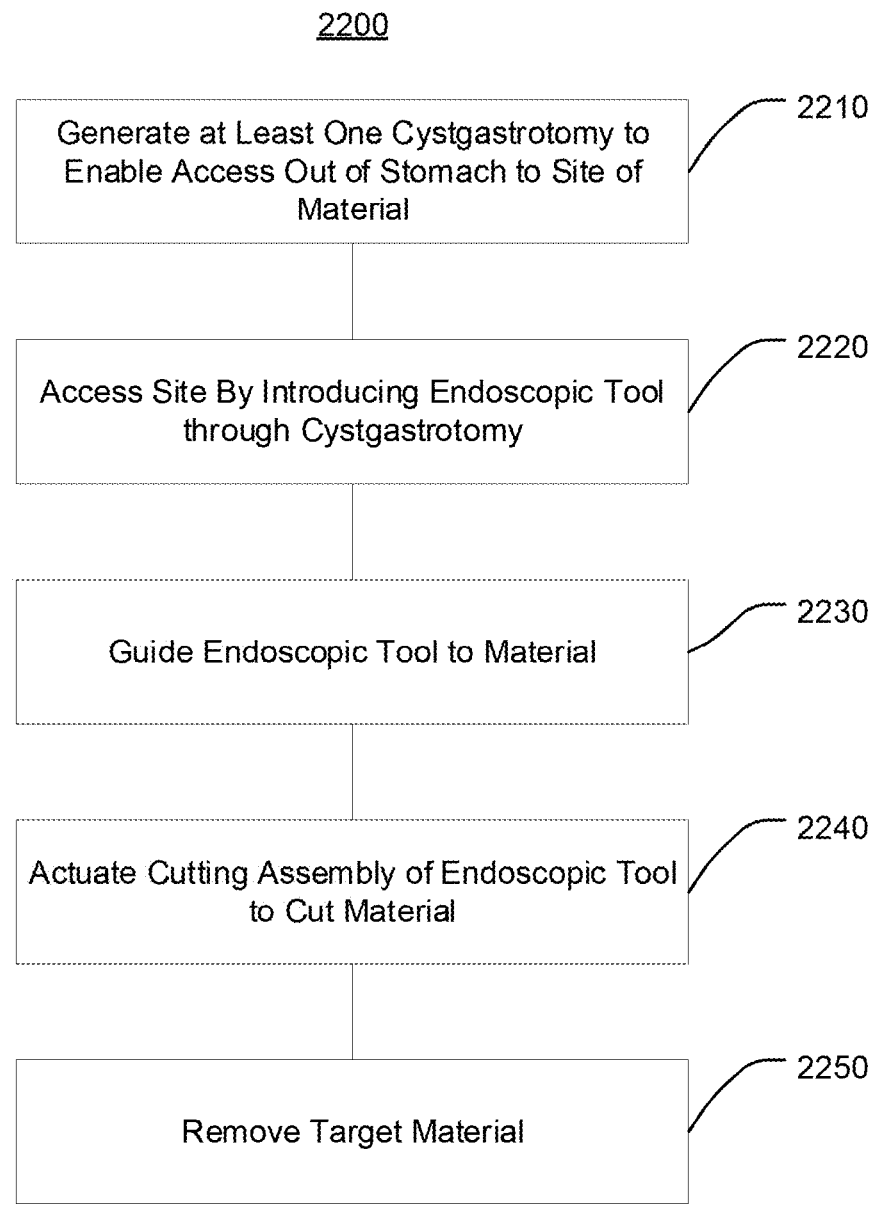
FIG. 22 is a flow diagram of a method of performing an endoscopic pancreatic procedure using an endoscopic tool.

Referring now to FIG. 22, a method 2200 of performing an endoscopic pancreatic procedure is shown. The method 2200 can be performed using various embodiments of endoscopic tools described herein, such as the ENDOROTOR. The method 2200 or steps thereof can be repeated, such as to address multiple sites having multiple materials of necrotic tissue to be removed, both inside and outside the pancreas.

At 2210, at least one cystgastrostomy is generated. The cystgastrostomy can be an opening generated on a cavity wall of a stomach of the subject. The cystgastrostomy can be used to provide access from the stomach into a pancreas of the subject or a body cavity proximate to the pancreas in which necrotic tissue or fluid collections from the pancreas are located. For example, the cystgastrostomy can be generated through the cavity wall of the stomach and a pancreas wall of a pancreas of a subject.

The at least one cystgastrostomy can be generated as a fistula, in some embodiments. The at least one fistula can be generated using a respective stent. The stent can include at least one of a luminal apposing metal stent (LAMS), a hot axios stent, or a plastic pig tail stent. In some embodiments, generating the fistula includes generating an opening through a stomach wall of the stomach and the pancreas wall. In some embodiments, generating the fistula includes generating an opening on the pancreas wall remote from the stomach wall, to enable access into the pancreas via a body cavity of the subject (rather than via a gastrointestinal pathway, such as via an esophagus).

At 2220, a site having material to be removed from the subject is accessed by introducing an endoscopic tool through the at least one cystgastrostomy. For example, the endoscopic tool can be introduced into the pancreas via the at least one cystgastrostomy. In some embodiments, the endoscopic tool is introduced into the pancreas via the esophagus, the stomach, and at least one cystgastrostomy providing a channel from the stomach into the pancreas. In some embodiments, the endoscopic tool is introduced into the pancreas via the body cavity and a cystgastrostomy on the pancreas wall remote from the stomach wall. In some embodiments, the site is external to the pancreas (e.g., associated with a fluid collection that has left the pancreas), and can be accessed through a cystgastrostomy generated on the stomach wall.

At 2230, the endoscopic tool is guided to the material. The material can be inflamed or necrotic material. Guiding the endoscopic tool can include using an image capture device of the endoscopic tool to identify the material, and moving a distal end of the endoscopic tool towards the material, such as to position the distal end adjacent to the material. The endoscopic tool can be guided to a plurality of locations of materials. The structure of the endoscopic tool can enable the endoscopic tool to follow a tortuous pathway to the material with reduced likelihood of the endoscopic tool (or endoscopic) breaking.

In some embodiments, a tissue plane corresponding to the material is identified. The tissue plane can include a portion of or extend from a cavity wall on which the necrotic tissue to be removed is located. The endoscopic tool (e.g., a distal end thereof) can be guided to be tangent or substantially tangent to a tissue plane of the material to be removed. For example, the distal end can be positioned such that a cutting window of a cutting assembly of the endoscopic tool at the distal end can be rotated to be facing the material with near or direct contact of the inner cannula (e.g., the distal end is within a threshold distance of the tissue plane less than or equal to ten millimeters). In some embodiments, the cutting window is adjusted to be within a threshold angle of tangent to the tissue plane. The threshold angle can be fifteen degrees. The threshold angle can be ten degrees. The threshold angle can be five degrees. The cutting window can be adjusted so that a rotation or reciprocation axis of the inner cannula is parallel to the tissue plane where the inner cannula contacts the tissue plane within the threshold angle. In some embodiments, the cutting window is positioned so that the tissue plane is between the cavity wall and the cutting window (e.g., to trap the necrotic tissue between the cavity wall and the cutter opening).

At 2240, the cutting assembly is actuated to cut the material. For example, the inner cannula can be rotated or reciprocated relative to the outer cannula while in contact with the material to cut the material. In some embodiments, a flexible torque component of the endoscopic tool that includes at least one of a flexible torque coil or a flexible torque rope is rotated by a drive assembly to rotate the inner cannula or a reciprocator coupled with the inner cannula that causes the inner cannula to reciprocate. The outer cannula can be rotated to adjust the cutting window. In some embodiments, the inner cannula is rotated at a rotation rate greater than or equal to 700 revolutions per minute and less than or equal to 2000 revolutions per minute, such as 1000 revolutions per minute.

At 2250, the endoscopic tool removes the material. The endoscopic tool can include an aspiration channel that applies vacuum through the endoscopic tool to the distal end (e.g., an opening at the distal end adjacent to the inner cannula) to remove the material through the aspiration channel. For example, a vacuum source can be applied to a first end of the aspiration channel (e.g., a first end located outside of the subject) to draw the material from an opening of the inner cannula at a second end of the aspiration channel through the aspiration channel and out of the first opening. The material can be cut and removed from a plurality of locations of the pancreas or external to the pancreas. The suction can be applied to the aspiration channel at a vacuum pressure greater than or equal to 200 mmHg and less than or equal to 750 mmHg. In some embodiments, the suction is applied while the cutting assembly is actuated and in contact with the material, which can allow for more rapid and efficient removal and suction of material as compared to separate removal and suction actions.

Figure 23:
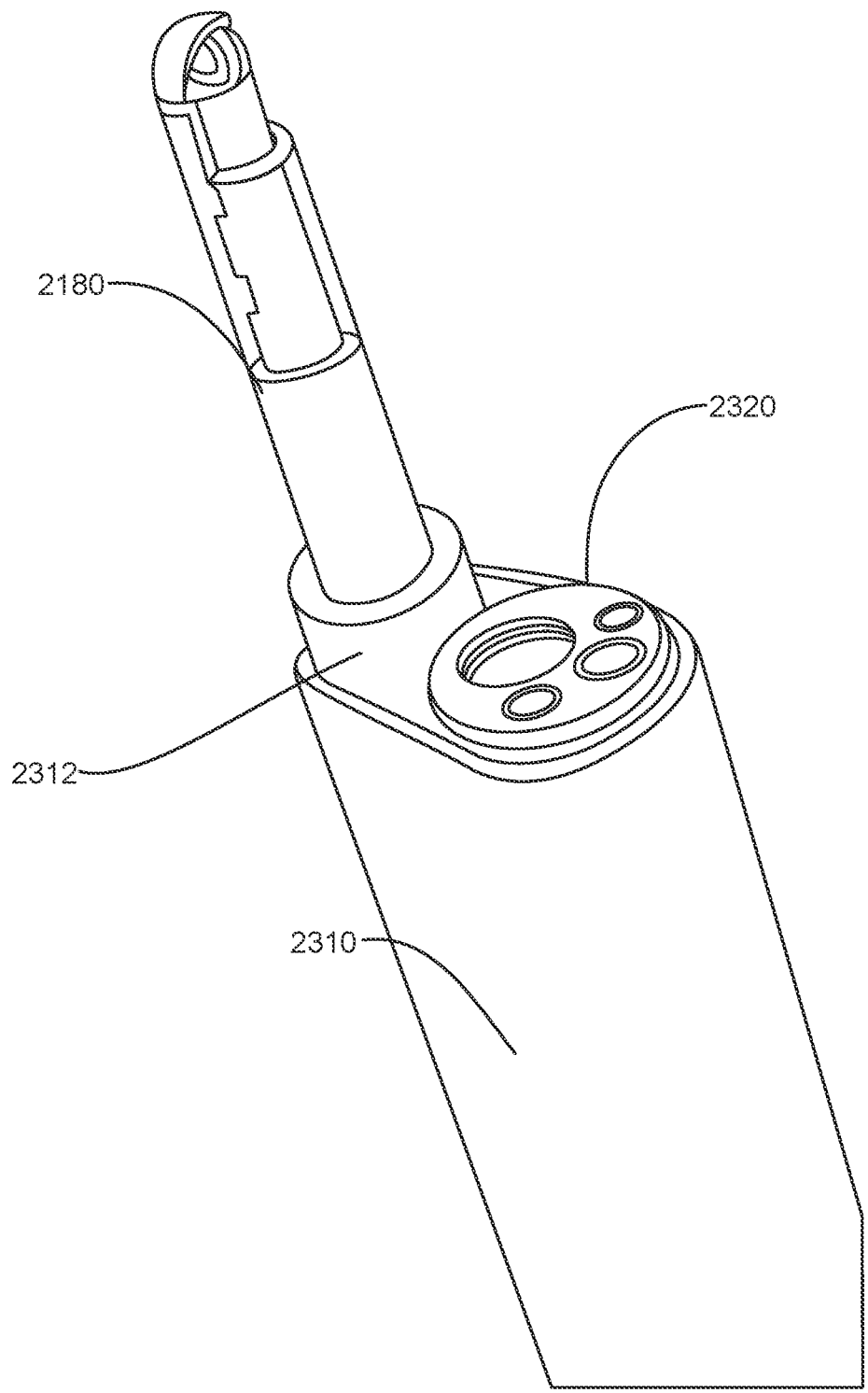
FIG. 23 is a schematic diagram of a sheath that couples an endoscopic instrument with an endoscope.

Referring now to FIG. 23, a sheath 2310 that can be used to couple the endoscopic tool 2180 to an endoscope 2320 is shown according to an embodiment of the present disclosure. The sheath 2310 can be used to enable the endoscopic tool 2380 to be outside of the endoscope 2320, such as to increase a range of movement of the endoscopic tool 2380 relative to the endoscope 2320. The sheath 2310 can include a working channel 2312 through which the endoscopic tool 2180 can be received and advanced. The sheath 2310 and working channel 2312 can be made from a flexible material, such as a plastic material. The working channel 2312 can have a relatively large diameter, such as a diameter of 3.8 mm or greater.

Figure 24:
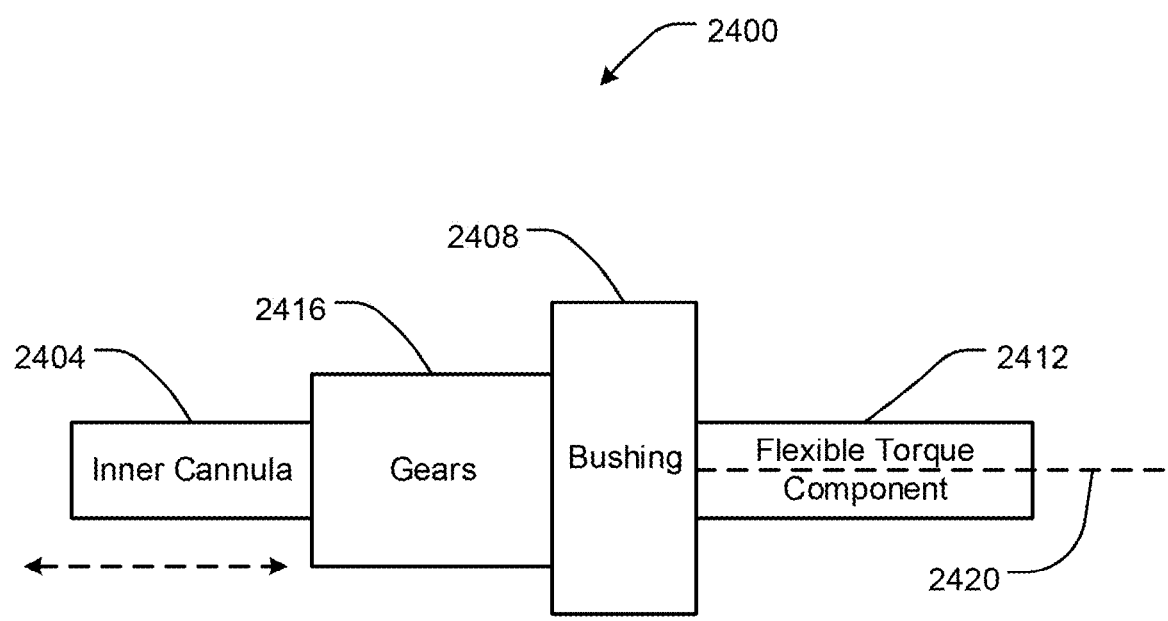
FIG. 24 is a schematic diagram of a reciprocator for reciprocating an inner cutter of an endoscopic tool.

Referring now to FIG. 24, a reciprocator 2400 for causing reciprocating movement of an inner cannula 2404 of an endoscopic tool (e.g., endoscopic tool 2180) is shown. The reciprocator 2400 can include a bushing 2408 coupled with a flexible torque component 2412 (e.g., flexible torque coil, flexible torque rope) of the endoscopic instrument, and at least one gear 2416 coupled with the inner cannula 2404 and the flexible torque component 2412 via the bushing 2408. The at least one gear 2416 can convert rotational movement of the flexible torque component 2412 about a rotational axis 2420 into linear motion of the inner cannula 2404. The linear motion may be along the rotational axis 2420 or offset from the rotational axis 2420.

Having now described some illustrative implementations, it is apparent that the foregoing is illustrative and not limiting, having been presented by way of example. In particular, although many of the examples presented herein involve specific combinations of method acts or system elements, those acts and those elements can be combined in other ways to accomplish the same objectives. Acts, elements and features discussed in connection with one implementation are not intended to be excluded from a similar role in other implementations or implementations.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

Any references to implementations or elements or acts of the systems and methods herein referred to in the singular can also embrace implementations including a plurality of these elements, and any references in plural to any implementation or element or act herein can also embrace implementations including only a single element. References in the singular or plural form are not intended to limit the presently disclosed systems or methods, their components, acts, or elements to single or plural configurations. References to any act or element being based on any information, act or element can include implementations where the act or element is based at least in part on any information, act, or element.

Any implementation disclosed herein can be combined with any other implementation or embodiment, and references to "an implementation," "some implementations," "one implementation" or the like are not necessarily mutually exclusive and are intended to indicate that a particular feature, structure, or characteristic described in connection with the implementation can be included in at least one implementation or embodiment. Such terms as used herein are not necessarily all referring to the same implementation. Any implementation can be combined with any other implementation, inclusively or exclusively, in any manner consistent with the aspects and implementations disclosed herein.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

Systems and methods described herein may be embodied in other specific forms without departing from the characteristics thereof. Further relative parallel, perpendicular, vertical or other positioning or orientation descriptions include variations within +/−10% or +/−10 degrees of pure vertical, parallel or perpendicular positioning. References to "approximately," "about" "substantially" or other terms of degree include variations of +/−10% from the given measurement, unit, or range unless explicitly indicated otherwise. Coupled elements can be electrically, mechanically, or physically coupled with one another directly or with intervening elements. Scope of the systems and methods described herein is thus indicated by the appended claims, rather than the foregoing description, and changes that come within the meaning and range of equivalency of the claims are embraced therein.

The term "coupled" and variations thereof includes the joining of two members directly or indirectly to one another. Such joining may be stationary (e.g., permanent or fixed) or moveable (e.g., removable or releasable). Such joining may be achieved with the two members coupled directly with or to each other, with the two members coupled with each other using a separate intervening member and any additional intermediate members coupled with one another, or with the two members coupled with each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

References to "or" can be construed as inclusive so that any terms described using "or" can indicate any of a single, more than one, and all of the described terms. A reference to "at least one of 'A' and 'B'" can include only 'A', only 'B', as well as both 'A' and 'B'. Such references used in conjunction with "comprising" or other open terminology can include additional items.

Modifications of described elements and acts such as variations in sizes, dimensions, structures, shapes and proportions of the various elements, values of parameters, mounting arrangements, use of materials, colors, orientations can occur without materially departing from the teachings and advantages of the subject matter disclosed herein. For example, elements shown as integrally formed can be constructed of multiple parts or elements, the position of elements can be reversed or otherwise varied, and the nature or number of discrete elements or positions can be altered or varied. Other substitutions, modifications, changes and omissions can also be made in the design, operating conditions and arrangement of the disclosed elements and operations without departing from the scope of the present disclosure.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

What is claimed is:

1. A method for removing materials from a subject, comprising:
    inserting an endoscope into the subject through an esophagus of the subject;
    introducing, via a cystogastrostomy opening through a wall of a stomach of the subject, an endoscopic tool coupled with the endoscope to access a site within the subject outside the stomach in the peri pancreatic and pancreatic space;
    actuating a torque component of the endoscopic tool to actuate a cutting assembly of the endoscopic tool to cut material at the site, the material associated with at least one of a pancreatic fluid collection in a pancreas of the subject or an extra-pancreatic fluid collection external to the pancreas; and
    applying suction to a first end of an aspiration channel of the endoscopic tool to remove the material through the aspiration channel, the aspiration channel defined by the torque component and extending from the first end to a second end at an opening of the cutting assembly.

2. The method of claim 1, wherein introducing the endoscopic tool comprises:
   identifying a tissue plane corresponding to the material;
   positioning the cutting assembly within a threshold distance of the tissue plane, the threshold distance less than or equal to ten millimeters; and
   adjusting a cutting window of the cutting assembly to be within a threshold angle of tangent to the tissue plane, the threshold angle less than or equal to fifteen degrees.

3. The method of claim 2, further comprising positioning the cutting window so that the tissue plane is between a tissue wall from which the tissue plane extends and the cutting window.

4. The method of claim 1, further comprising generating at least one cystogastrostomy opening to enable access to the site by using at least one of a luminal apposing metal stent (LAMS), a fully covered metal stent, or at least one plastic pig tail stent.

5. The method of claim 1, further comprising providing the endoscopic tool through at least one of a working channel or an accessory channel of the endoscope.

6. The method of claim 1, further comprising coupling the endoscopic tool to the endoscope using a sheath external to the endoscope.

7. The method of claim 1, wherein actuating the cutting assembly comprises at least one of rotating or reciprocating an inner cannula of the endoscopic tool, the inner cannula defining the opening through which the material is removed.

8. The method of claim 7, wherein the inner cannula is disposed within an outer cannula.

9. The method of claim 7, wherein rotating the inner cannula comprises rotating the inner cannula at a rotation rate greater than or equal to 700 revolutions per minute and less than or equal to 5000 revolutions per minute.

10. The method of claim 1, wherein a diameter of the endoscopic instrument is greater than 3 mm and less than 7 mm.

11. The method of claim 1, further comprising using an image capture device of the endoscope to detect one or more images of the material.

12. The method of claim 1, further comprising applying the suction to the aspiration channel at a vacuum pressure greater than or equal to 200 mmHg and less than or equal to 750 mmHg.

13. The method of claim 1, further comprising applying the suction while actuating the cutting assembly when the cutting assembly is adjacent to the site.

14. The method of claim 1, further comprising introducing the endoscope into the stomach of the subject from the esophagus and introducing the endoscopic tool from the stomach through the cavity wall.

* * * * *